United States Patent
Ohara et al.

(10) Patent No.: US 12,354,297 B2
(45) Date of Patent: Jul. 8, 2025

(54) CONTROL APPARATUS, ENDOSCOPE POSITIONING STATE DETERMINATION METHOD, AND NON-TRANSITORY RECORDING MEDIUM

(71) Applicant: OLYMPUS CORPORATION, Tokyo (JP)

(72) Inventors: Jin Ohara, Hachioji (JP); Yuichiro Hashimoto, Hachioji (JP); Keigo Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 357 days.

(21) Appl. No.: 17/888,682

(22) Filed: Aug. 16, 2022

(65) Prior Publication Data

US 2022/0392102 A1 Dec. 8, 2022

Related U.S. Application Data

(63) Continuation of application No. PCT/JP2020/006308, filed on Feb. 18, 2020.

(51) Int. Cl.
*G06K 9/00* (2022.01)
*A61B 1/12* (2006.01)
(Continued)

(52) U.S. Cl.
CPC ............... *G06T 7/70* (2017.01); *A61B 1/123* (2013.01); *A61B 90/70* (2016.02); *G06T 7/90* (2017.01);
(Continued)

(58) Field of Classification Search
CPC .......... A61L 2202/24; A61L 2/28; A61L 2/18; A61L 2/186; A61L 2202/14; A61L 2202/17
See application file for complete search history.

(56) References Cited

U.S. PATENT DOCUMENTS

2009/0241987 A1* 10/2009 Serizawa ............. A61L 2/18
134/1
2011/0097248 A1* 4/2011 Tomita ............... A61L 2/18
422/292
(Continued)

FOREIGN PATENT DOCUMENTS

CN 1964665 A 5/2007
CN 108523801 A 9/2018
(Continued)

OTHER PUBLICATIONS

International Search Report dated Apr. 14, 2020 received in PCT/JP2020/006308.

*Primary Examiner* — Hadi Akhavannik
(74) *Attorney, Agent, or Firm* — Scully, Scott, Murphy & Presser, P.C.

(57) ABSTRACT

A control unit of a reprocessor main body includes a processor, the processor being configured to acquire a plurality of observation images, image pickup angles of which regarding a positioning state of an endoscope positioned in an endoscope reprocessor are different, select an image showing a first part that is a predetermined part inside the endoscope reprocessor and a second part that is a predetermined part of the endoscope, and determine whether the second part is included in a predetermined range from the first part.

20 Claims, 17 Drawing Sheets

(51) Int. Cl.
  *A61B 90/70* (2016.01)
  *G06T 7/70* (2017.01)
  *G06T 7/90* (2017.01)
(52) U.S. Cl.
  CPC ............... *A61B 2090/701* (2016.02); *G06T 2207/20081* (2013.01)

(56) References Cited

U.S. PATENT DOCUMENTS

| | | | |
|---|---|---|---|
| 2012/0073614 A1* | 3/2012 | Otani | A61L 2/186 134/56 R |
| 2012/0108902 A1* | 5/2012 | Frassica | A61B 1/00133 600/114 |
| 2016/0249794 A1* | 9/2016 | Suzuki | B08B 3/08 134/169 C |
| 2018/0116760 A1* | 5/2018 | Blumenkranz | A61B 34/30 |
| 2018/0267489 A1 | 9/2018 | Tango et al. | |
| 2018/0296303 A1* | 10/2018 | Wellens | A61L 2/24 |
| 2018/0304315 A1* | 10/2018 | Connelly | B08B 3/04 |
| 2018/0310815 A1 | 11/2018 | Tezuka et al. | |
| 2019/0191968 A1* | 6/2019 | Tsumaru | G02B 7/007 |
| 2019/0290796 A1* | 9/2019 | Ma | G16H 40/20 |
| 2020/0260943 A1* | 8/2020 | Nishi | A61B 1/121 |

FOREIGN PATENT DOCUMENTS

| | | |
|---|---|---|
| DE | 102017111628 A1 | 11/2018 |
| EP | 3 384 823 A1 | 10/2018 |
| JP | 64-009603 U1 | 1/1989 |
| JP | H10-296194 A | 11/1998 |
| JP | 2002-272684 A | 9/2002 |
| JP | 2006-230492 A | 9/2006 |
| JP | 2009-039207 A | 2/2009 |
| JP | 2009-066291 A | 4/2009 |
| JP | 4611054 B2 | 1/2011 |
| JP | 2011-193982 A | 10/2011 |
| JP | 2013-106790 A | 6/2013 |
| JP | 5566494 B2 | 8/2014 |
| JP | 2014-226153 A | 12/2014 |
| JP | 2018-130473 A | 8/2018 |
| JP | 2018-153872 A | 10/2018 |
| WO | 2017/188044 A1 | 11/2017 |
| WO | 2019/087599 A1 | 5/2019 |
| WO | 2019/203010 A1 | 10/2019 |

* cited by examiner

CONTROL APPARATUS, ENDOSCOPE POSITIONING STATE DETERMINATION METHOD, AND NON-TRANSITORY RECORDING MEDIUM

CROSS REFERENCE TO RELATED APPLICATION

This application is a continuation application of PCT/JP2020/006308 filed on Feb. 18, 2020, the entire contents of which are incorporated herein by this reference.

BACKGROUND OF THE INVENTION

1. Field of the Invention

The present invention relates to a control apparatus for determining whether an endoscope is appropriately positioned inside a treatment tank of an endoscope reprocessor, an endoscope positioning state determination method, and a non-transitory recording medium.

2. Description of the Related Art

Nowadays, there are endoscope reprocessors that perform reprocessing such as cleaning/disinfection on an endoscope used in a subject. In the case of performing reprocessing using such an endoscope reprocessor, the endoscope is positioned inside a treatment tank in a wound state. In this case, when a setting state of the endoscope (such as a wound state of an insertion section) described in a manual or the like is followed, a medicinal solution may entirely cover a surface of the endoscope, and appropriate reprocessing may be guaranteed. Accordingly, there is a demand for a technique of determining whether an endoscope reprocessor is used in a state where an endoscope is appropriately positioned such that reprocessing is correctly performed.

For example, as a technique for determining a setting state of an endoscope, Japanese Patent Application Laid-Open Publication No. 2006-230492 discloses an endoscope cleaning apparatus where an endoscope detection sensor configured to detect that an endoscope is housed and positioned at a predetermined position is provided at a predetermined position on a side surface of a tank main body. According to the technique of Japanese Patent Application Laid-Open Publication No. 2006-230492, the endoscope detection sensor includes a pair of optical sensors including a light emission unit configured to emit light and a light reception unit configured to receive light from the light emission unit.

SUMMARY OF THE INVENTION

A control apparatus according to an aspect of the present invention includes a processor, where the processor is configured to acquire a plurality of observation images, image pickup angles of which regarding a positioning state of an endoscope positioned in an endoscope reprocessor are different, select an image showing a first part that is a predetermined part inside the endoscope reprocessor and a second part that is a predetermined part of the endoscope, and determine whether the second part is included in a predetermined range from the first part.

An endoscope positioning state determination method according to one aspect of the present invention includes: acquiring a plurality of observation images, image pickup angles of which regarding a positioning state of an endoscope positioned in an endoscope reprocessor are different; and determining, in order from one of the plurality of observation images that is acquired last in a time series, whether a second part is included in a predetermined range from a first part that is a predetermined part inside the endoscope reprocessor.

A non-transitory recording medium according to an aspect of the present invention, records a program for causing a computer to: acquire a plurality of observation images, image pickup angles of which regarding a positioning state of an endoscope positioned in an endoscope reprocessor are different; and determine, in order from one of the plurality of observation images that is acquired last in a time series, whether a second part is included in a predetermined range from a first part that is a predetermined part inside the endoscope reprocessor.

DETAILED DESCRIPTION OF THE PREFERRED EMBODIMENTS

Hereinafter, an embodiment of the present invention will be described with reference to the drawings.

Figure 1:
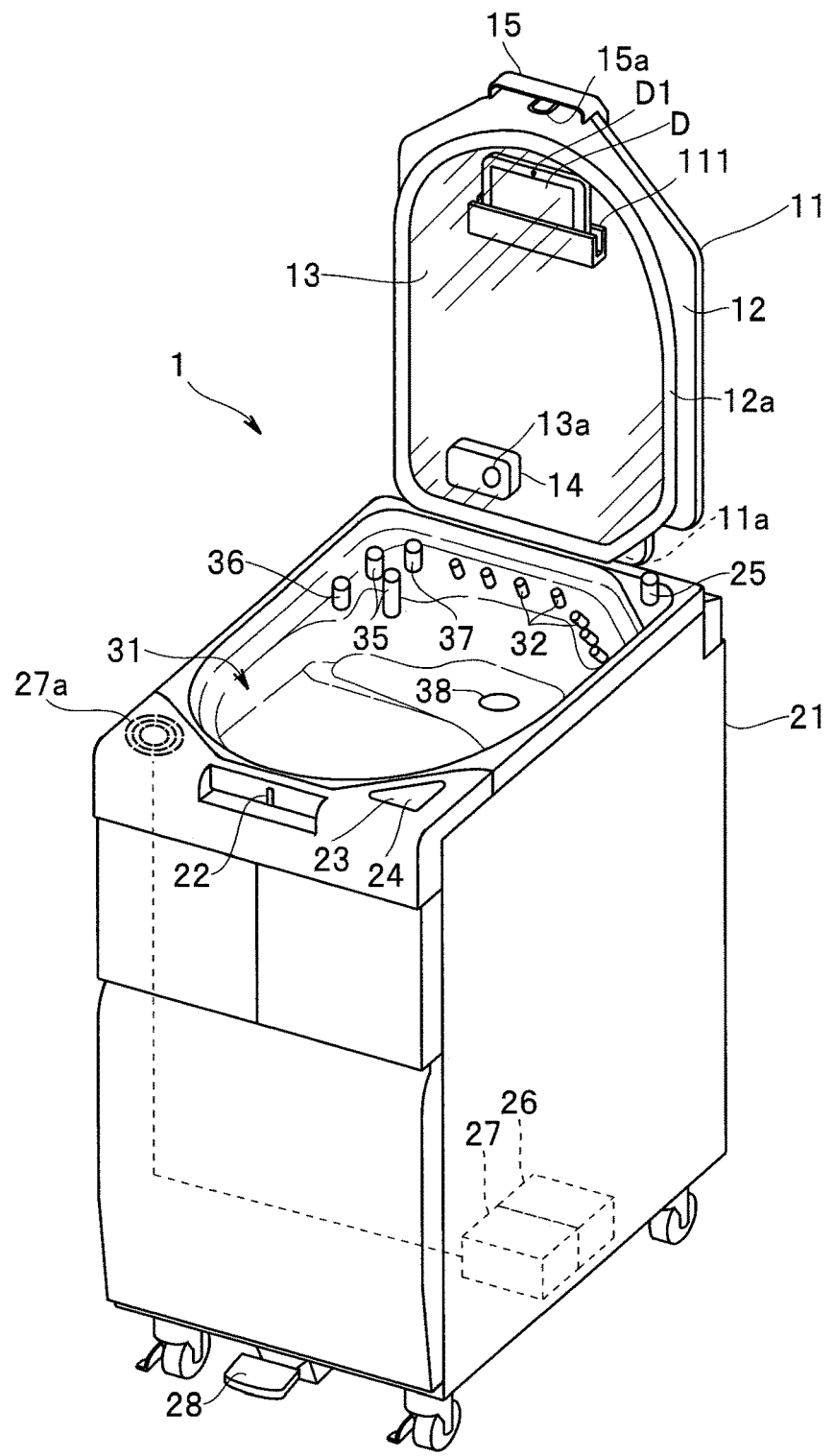
FIG. 1 is a perspective view of an endoscope reprocessor.
Figure 2:
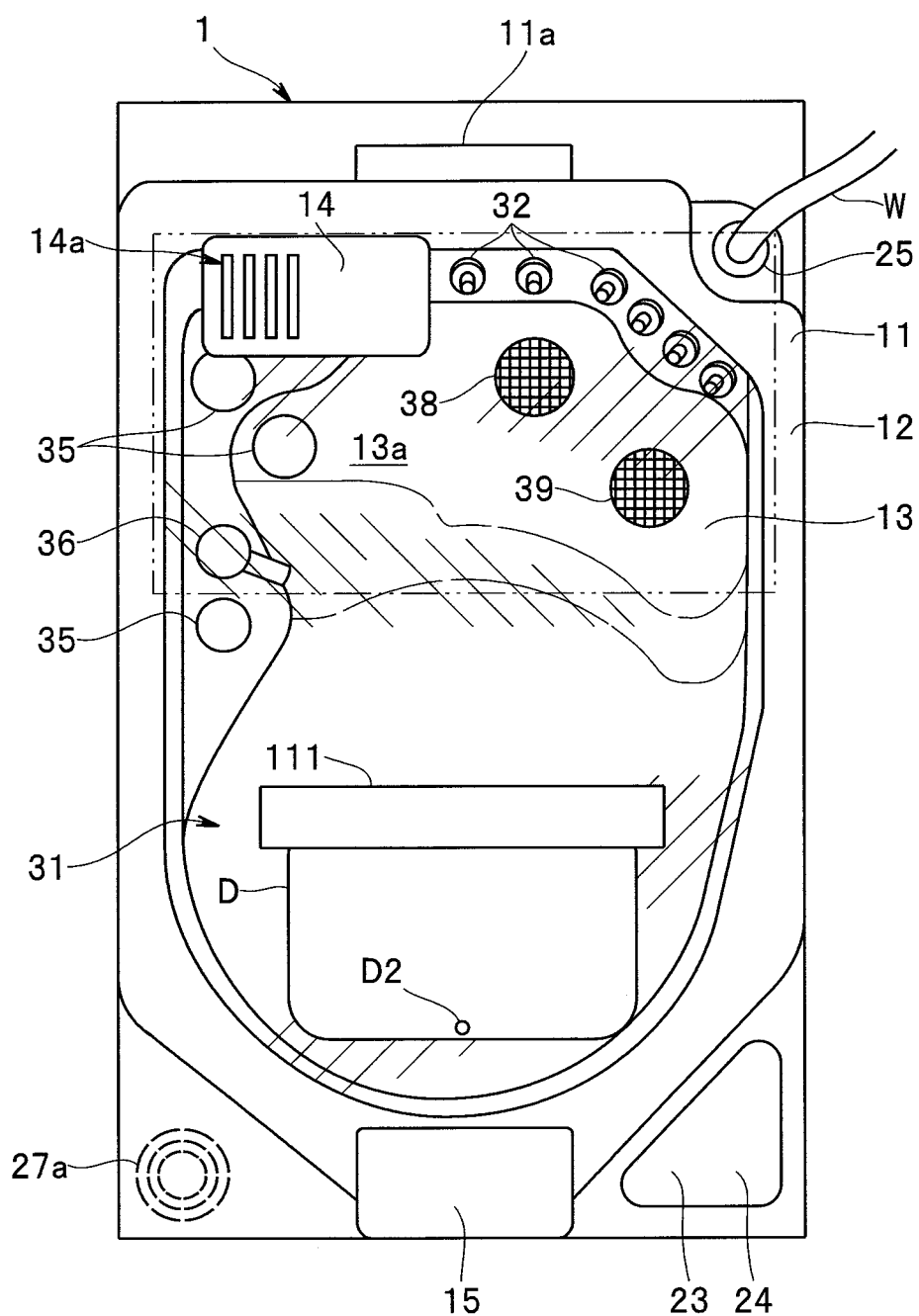
FIG. 2 is a top view of the endoscope reprocessor.
Figure 3:
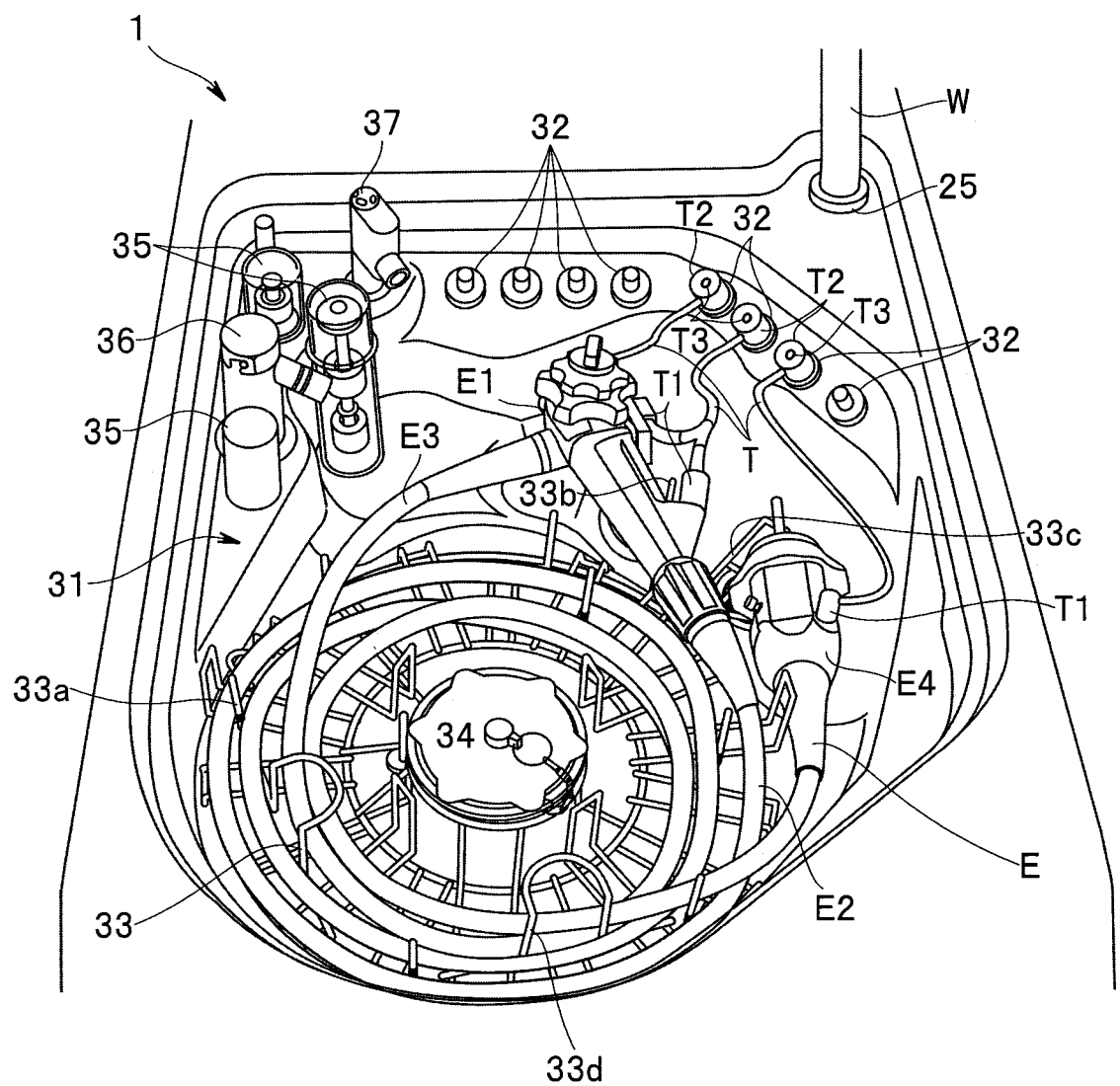
FIG. 3 is an explanatory diagram showing a state where an endoscope is positioned in a treatment tank of the endoscope reprocessor.
Figure 4:
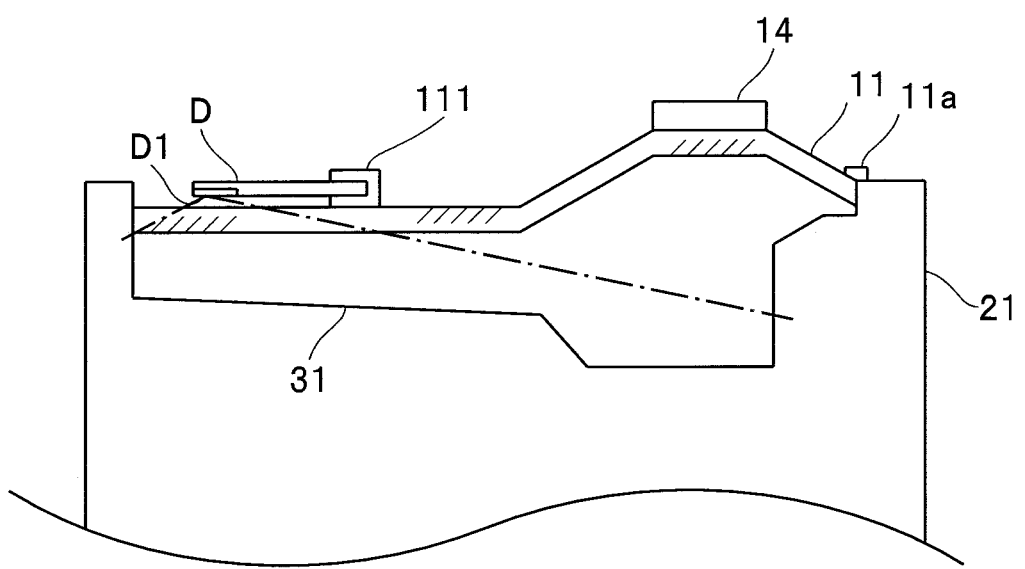
FIG. 4 is an explanatory diagram for describing positioning of a terminal holding section of the endoscope reprocessor.

FIG. 1 is a perspective view of an endoscope reprocessor 1 according to an embodiment of the present invention. FIG. 2 is a top view of the endoscope reprocessor 1 according to the embodiment of the present invention. FIG. 3 is an explanatory diagram for describing a state where an endoscope E is positioned in a treatment tank 31 of the endoscope reprocessor 1 according to the embodiment of the present invention.

The endoscope reprocessor 1 is an apparatus that performs reprocessing on the endoscope E that is contaminated, components or accessories of the endoscope E, and the like. Reprocessing here is not particularly limited, and may be any of, or a combination of, rinsing with water, cleaning to remove stains due to organic matters or the like, disinfection to inactivate predetermined microorganisms, or sterilization to eliminate or kill all microorganisms. Furthermore, the endoscope reprocessor 1 may be used to perform reprocessing on tubular medical equipment, such as dilators or endoscope sheaths.

Note that in the following description, a downward direction indicates a gravity direction, an upward direction indicates a direction opposite to the gravity direction, and high/low indicates a height relationship in the gravity direction.

In the present embodiment, the endoscope reprocessor 1 includes a top cover 11 as a cover including a cover panel 13 that is a transmission section, a reprocessor main body 21, and a terminal holding section 111 provided on the top cover 11. The terminal holding section 111 holds an observation terminal D that receives an observation wave.

Figure 17:
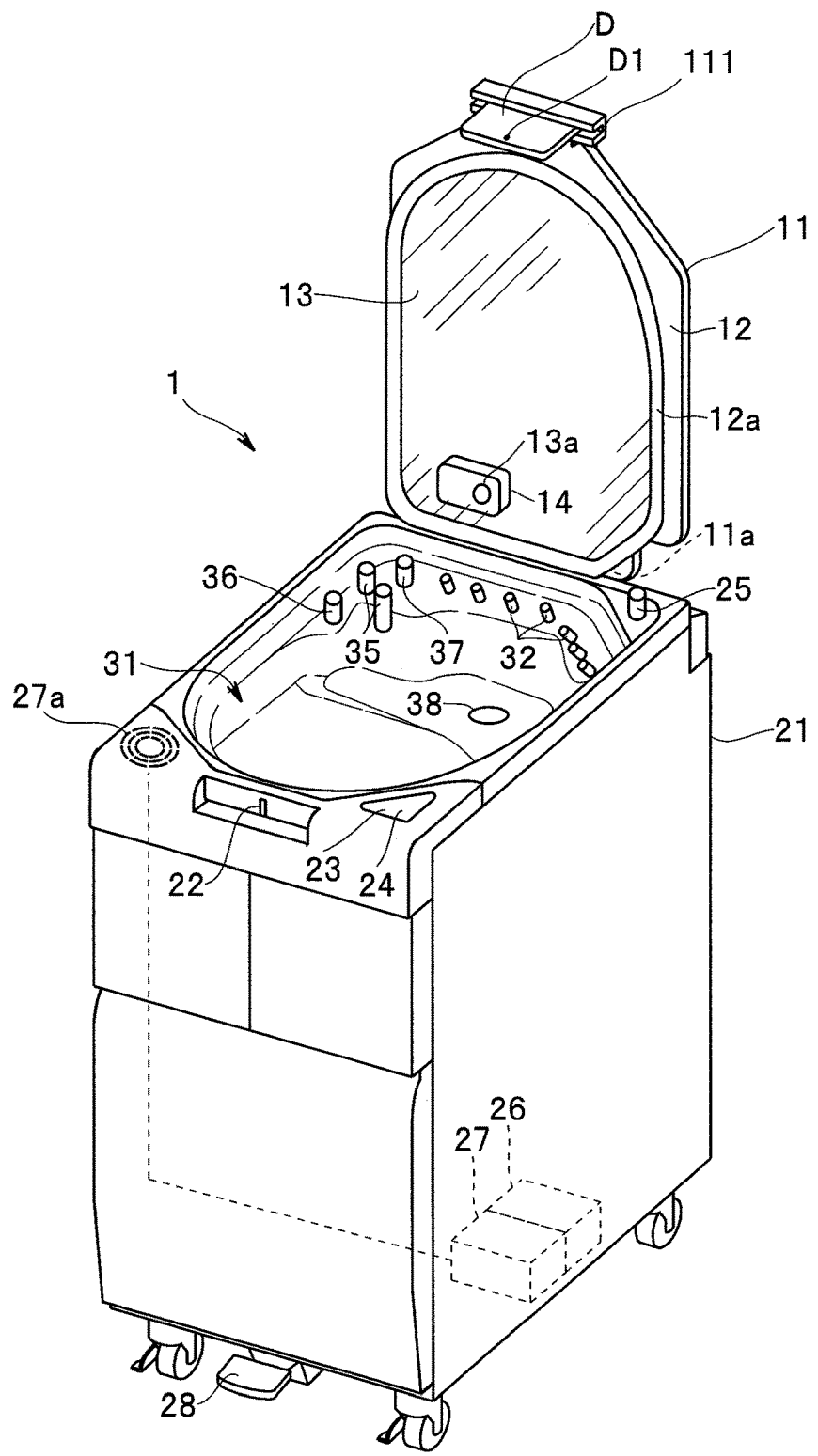
FIG. 17 is a perspective view of an endoscope reprocessor according to a first modification.

In FIGS. 1 and 2, the terminal holding section 111 holds the observation terminal D in such a way that the observation terminal D is disposed on a surface of the top cover 11, but the present invention is not limited to such a case. For example, as shown in FIG. 17, the observation terminal D may be attached to an end of the top cover 11 to be exposed from the top cover 11. In this case, the terminal holding section 111 for holding the observation terminal D is provided on an end surface at the other end of the top cover 11, at a predetermined angle, for example.

The top cover 11 is positioned with a back surface facing the treatment tank 31 of the reprocessor main body 21. The top cover 11 allows opening/closing of the treatment tank 31 by rotation around a hinge 11a. In other words, one end of the top cover 11 is connected to the reprocessor main body 21 by the hinge 11a, and the other end is rotated around the one end. When in a closed state, the top cover 11 covers the treatment tank 31. The top cover 11 includes a cover frame 12, the cover panel 13 that is a transmission section, a gas filter 14, and a finger hooking section 15. The top cover 11 may be provided with a gyrosensor, and may be capable of transmitting angular velocity information to the observation terminal D.

The cover frame 12 is provided extending along a periphery portion of the top cover 11. A material of the cover frame 12 is not particularly limited, and metal or resin may be cited as an example. The cover frame 12 includes, on a back surface, a packing 12a that is provided extending along a top edge portion of the treatment tank 31. When the top cover 11 is placed in the closed state, the packing 12a comes into close contact with the top edge portion of the treatment tank 31.

The cover panel 13 has a light transmitting property. As a transmitting material for forming the cover panel 13, resin or ceramic may be cited as an example. As the resin, polycarbonate having chemical resistance and a visible light transmitting property may be cited as an example. The cover panel 13 is provided inside the cover frame 12. Although not particularly limited, the cover panel 13 may include a cover discharge port 13a at a part, on the one side, bulging in a dome shape.

The gas filter 14 is formed of a filter medium container and a filter medium contained in the filter medium container, and is removably attached to the cover discharge port 13a. The gas filter 14 includes a filter discharge port 14a at an upper portion (FIG. 2). The gas filter 14 takes gas from the treatment tank 31 through the cover discharge port 13a, and discharges gas subjected to filtering for deodorization or the like through the filter discharge port 14a.

The finger hooking section 15 is provided continuously to the other end side of the cover frame 12 to allow a user to hook his/her finger thereon. A catch 15a is provided inside the finger hooking section 15.

The reprocessor main body 21 includes a lock section 22, a display unit 23 as a notification unit, an operation unit 24, a water supply hose connection port 25, a communication unit 26, a control unit 27 as a control apparatus, and the treatment tank 31.

The lock section 22 is provided on the other end side of an upper portion of the reprocessor main body 21. The lock section 22 engages with the catch 15a or releases engagement with the catch 15a by being controlled by the control unit 27. When the lock section 22 engages with the catch 15a, the top cover 11 is locked in the closed state. When the lock section 22 is coupled to a foot panel 28, engagement with the catch 15a may be released by the foot panel.

The display unit 23 is provided at the upper portion of the reprocessor main body 21, at a corner portion on the other end side. The display unit 23 includes a display panel, and issues various notifications to the user by being controlled by the control unit 27.

The operation unit 24 includes an instruction input button, and allows input of various instructions to the endoscope reprocessor 1.

The water supply hose connection port 25 is connected to a tap by a water supply tube W.

The communication unit 26 is connected to the control unit 27, and is capable of communicating with the observation terminal D in a wired or wireless manner by being controlled by the control unit 27. The communication unit 26 may also be able to communicate with an external apparatus via a network.

The control unit 27 controls each unit of the endoscope reprocessor 1. The control unit 27 includes a processor and a memory, and is capable of executing various programs stored in the memory. Functions of the control unit 27 are implemented by reading and executing the programs stored in the memory.

The control unit 27 is connected to the observation terminal D via the communication unit 26. When a determination result indicating an abnormality is inputted from the observation terminal D, the control unit 27 notifies the user of the abnormality. An abnormality notification may be a display of warning on the display unit 23, or may be output of a warning sound from a speaker, not shown. Furthermore, when the determination result indicating an abnormality is inputted from the observation terminal D, the control unit 27 may perform control to stop reprocessing.

The control unit 27 is connected to a reading apparatus 27a for RFID (radio frequency identification). For example, the reading apparatus 27a is provided on the other end side at the upper portion of the reprocessor main body 21, at a corner portion on an opposite side from the display unit 23 across the treatment tank 31.

The reading apparatus 27a is capable of communicating with an RFID tag (not shown) provided to a scope connector E4 or the like of the endoscope E, in a non-contact manner using radio waves or electromagnetic waves.

As shown in FIG. 3, the treatment tank 31 is provided at an upper portion of the reprocessor main body 21. As shown in FIG. 3, when the top cover 11 is in an open state, the treatment tank 31 is exposed to outside. The treatment tank 31 has a recessed shape so that the endoscope E to be subjected to reprocessing may be housed and liquid, such as a cleaning solution, a disinfecting solution or a rinsing liquid, may be stored. As shown in FIGS. 2 and 3, the treatment tank 31 includes air/water feeding connectors 32, a holding net 33, a cleaning case 34, water level gauges 35, a medicinal solution nozzle 36, a water supply circulation nozzle 37, a circulation port 38, and a liquid discharge port 39.

In the treatment tank 31, a cleaning tube T connects the reprocessor main body 21 and the endoscope E. The cleaning tube T includes an endoscope-side connector T1 that is connected to the endoscope E, and a reprocessor-side connector T2 that is connected to the reprocessor main body 21. An ejection port T3 from which liquid is ejected in a liquid passing state is provided to the reprocessor-side connector T2.

For example, the endoscope E includes an endoscope operation section E1, an insertion section E2 having an elongated shape that extends from the endoscope operation section E1 to a distal end side, a universal cord E3 extending from the endoscope operation section E1, and the scope connector E4 provided extending from a distal end side of the universal cord E3. The endoscope-side connectors T1 are connected to the endoscope operation section E1 and the scope connector E4.

The air/water feeding connectors 32 are provided in a wall of the treatment tank 31. The reprocessor-side connector T2 is connected to the air/water feeding connector 32. FIG. 3 shows eight air/water feeding connectors 32, but the number of air/water feeding connectors 32 is not limited to eight. The air/water feeding connector 32 is connected to the circulation port 38 by a conduit. When the control unit 27 drives a circulation pump, the air/water feeding connector 32 feeds liquid taken in from the circulation port 38 to the endoscope E. Furthermore, when the control unit 27 drives an air compressor, the air/water feeding connector 32 feeds air taken in from atmosphere to the endoscope E.

The holding net 33 is attached to a bottom portion of the treatment tank 31. A material of the holding net is not particularly limited, and metal or resin may be cited as an example. The holding net 33 includes an index pin 33a including a mark for indicating a height of a disinfecting liquid level, an operation section receiving section 33b where the endoscope operation section E1 is positioned, a scope connector receiving section 33c where the scope connector E4 is positioned, and a hook 33d where the insertion section E2 and the universal cord E3 are hooked. The user positions the endoscope operation section E1 on the operation section receiving section 33b, positions the scope connector E4 on the scope connector receiving section 33c, and winds the insertion section E2 and the universal cord E3 to pass on an inside of the hook 33d. The user causes the endoscope E to be held by the holding net 33 at below the mark of the index pin 33a so as not to rise above the disinfecting liquid level.

A setting state of such an endoscope E is described in a manual for the endoscope E, a manual for the endoscope reprocessor 1, or the like, in relation to each type of endoscope E. In other words, to perform appropriate reprocessing on the endoscope E, an appropriate positioning state is set for each type of endoscope E such that positioning is performed in such a way that parts (especially, the insertion section E2 and the like) wound around on the holding net 33 and the like do not come into close contact with each other.

The cleaning case 34 is attached to a center portion of the holding net 33. Accessories removed from the endoscope E, such as an air/water feeding button, a suction button, and a cap, are housed in the cleaning case 34. A lower portion of the cleaning case 34 is connected to a bottom portion connector provided at a bottom portion of the reprocessor main body 21. Air or water is fed from the bottom portion connector to the cleaning case 34 by being controlled by the control unit 27. The accessories are not particularly limited, and for example, the suction button and the air/water feeding button that are attached to the endoscope E at the time of use and removed from the endoscope E at the time of reprocessing, or a distal end cover that covers a distal end portion of the endoscope E may be cited as examples.

The water level gauge 35 checks a level of liquid in the cleaning tank, and outputs a check result to the control unit 27.

The medicinal solution nozzle 36 is provided at a terrace section that is provided at a periphery portion inside the treatment tank 31, at a position that is one step higher. The medicinal solution nozzle 36 is connected to a medicinal solution tank inside the reprocessor main body 21, and discharges a medicinal solution in the medicinal solution tank to the treatment tank 31 by driving of a medicinal solution pump by the control unit 27.

The water supply circulation nozzle 37 is provided at the terrace section. The water supply circulation nozzle 37 is connected to the circulation port 38 by a conduit. When the control unit 27 drives the circulation pump, the water supply circulation nozzle 37 discharges liquid taken in from the circulation port 38 into the treatment tank 31. Furthermore, the water supply circulation nozzle 37 discharges water supplied from the water supply tube W into the treatment tank 31 via the water supply hose connection port 25, by being controlled by the control unit 27.

Each of the circulation port 38 and the liquid discharge port 39 is provided at the bottom portion of the treatment tank 31, and a mesh filter is attached to each of the circulation port 38 and the liquid discharge port 39 (FIG. 2). The circulation port 38 takes in liquid in the treatment tank 31. The liquid discharge port 39 is connected to external liquid discharge means, and discharges liquid in the treatment tank 31 to outside. Furthermore, the liquid discharge port 39 is capable of being connected to the medicinal solution tank by being controlled by the control unit 27. When the liquid discharge port 39 is connected to the medicinal solution tank, the medicinal solution used in the treatment tank 31 gets collected in the medicinal solution tank.

An example of the medicinal solution used by the endoscope reprocessor 1 is peracetic acid solution. The peracetic acid solution is prepared inside the endoscope reprocessor 1 to a predetermined concentration by dilution of a stock solution with water supplied through the water supply tube W. The medicinal solution is stored in the medicinal solution tank, and is discharged into the treatment tank 31 through the medicinal solution nozzle 36 at the time of disinfection of the endoscope E. After being used to disinfect the endoscope E, the medicinal solution is collected into the medicinal solution tank to be used for next reprocessing. A concentration of the medicinal solution decreases according to the number of used days and the number of used times.

The terminal holding section 111 is provided on a surface side of the top cover 11, opposite from a back surface side (FIG. 2). A material of the terminal holding section is not particularly limited, and metal or resin may be cited as an example. The terminal holding section 111 is configured such that the observation terminal D may be held at a position that allows observation of inside of the treatment tank 31 through the cover panel 13. In other words, the terminal holding section 111 is disposed on an outer surface of the top cover 11.

Figure 5:
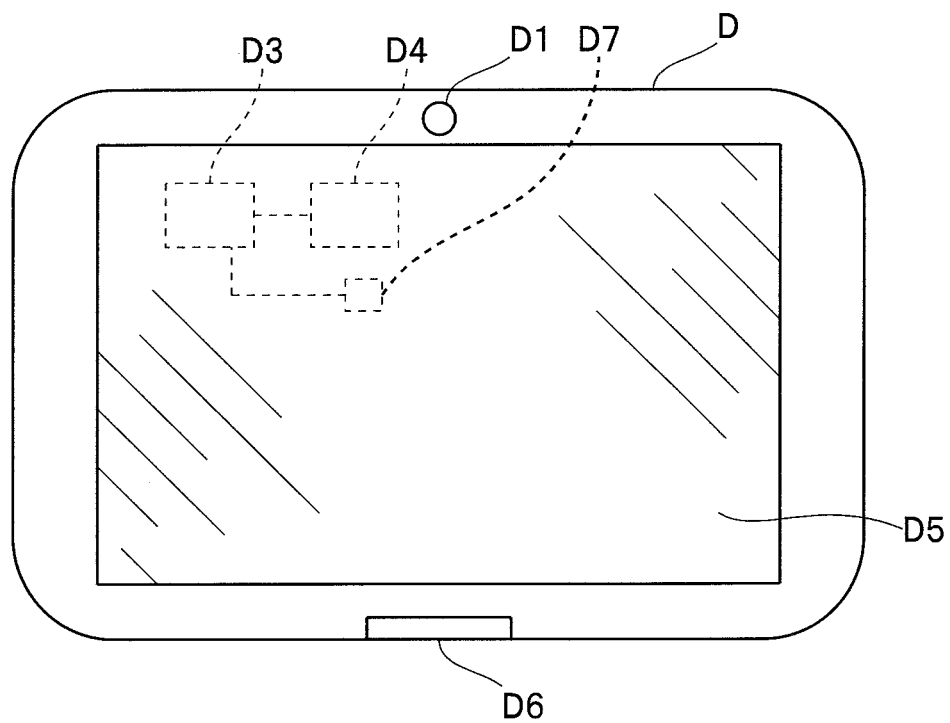
FIG. 5 is a front view of an observation terminal of the endoscope reprocessor.
Figure 6:
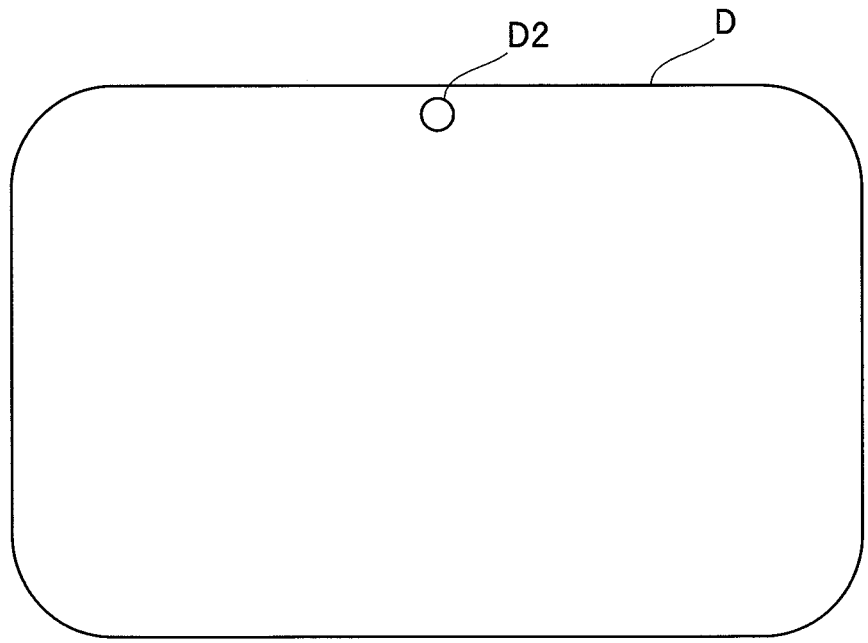
FIG. 6 is a rear view of the observation terminal of the endoscope reprocessor.

FIG. 5 is a front view of the observation terminal D of the endoscope reprocessor 1 according to the embodiment of the present invention. FIG. 6 is a rear view of the observation terminal D of the endoscope reprocessor 1 according to the embodiment of the present invention.

As shown in FIGS. 5 and 6, the observation terminal D is a tablet personal digital assistant, for example. The observation terminal D includes an observation unit D1, a control unit D3 as a control apparatus, and a notification unit D5. The observation terminal D preferably includes an observation unit D2, a communication unit D4, an external connection connector D6, or a gyrosensor D7.

The observation unit D1 is provided on a front surface of the observation terminal D. The observation unit D2 is provided on a back surface of the observation terminal D. A configuration of a known camera may be used as the observation unit D1 and D2. The observation unit D1 and D2 includes an image pickup device including a CMOS, a CCD or the like, and picks up an image of outside, and outputs a picked-up image to the control unit D3 as an observation image P. The observation unit D1 and D2 may include a wide angle lens. The wide angle lens may be fixed to the observation terminal D, or may be removable from the observation terminal D.

In other words, the observation unit D1 as a reception unit receives light that is reflected inside the treatment tank 31 and that is transmitted through the cover panel 13. Light here is not limited to visible light, and may be far infrared light, infrared light, or ultraviolet light.

The control unit D3 includes a processor and a memory, and controls operation of each unit in the observation terminal D.

The control unit D3 may determine an endoscope positioning state based on a picked-up image or moving image, or determination may be performed by an external apparatus instead of by the observation terminal D. In the case where determination is performed by an external apparatus, the picked-up image is outputted to the external apparatus via the communication unit D4 or the external connection connector D6 described later. As the external apparatus, a smartphone, a tablet, a personal computer, a reprocessor, or a cloud may be cited as an example.

Furthermore, a determination result from the control unit D3 or the external apparatus may be outputted to the display unit D5 of the observation terminal D or to an external apparatus. The external apparatus as an output destination of the determination result may be a smartphone, a tablet, a personal computer, a reprocessor, or an alarm apparatus.

In an example where output to an external apparatus is to be performed, the communication unit D4 performs communication with the communication unit 26, and outputs the determination result to the control unit 27 of the reprocessor main body 21, for example. In the case where the determination result that is inputted indicates "incorrect positioning", the control unit 27 may execute a program to display a warning on the display unit 23 of the reprocessor main body 21 or to lock the operation unit 24 to prevent reprocessing from being started, for example.

The display unit D5 is capable of displaying various types of information on a display panel by being controlled by the control unit D3. The display unit D5 may display the determination result. A touch panel overlaps the display panel of the display unit D5, and various instructions may be inputted by touch operation.

Figure 7:
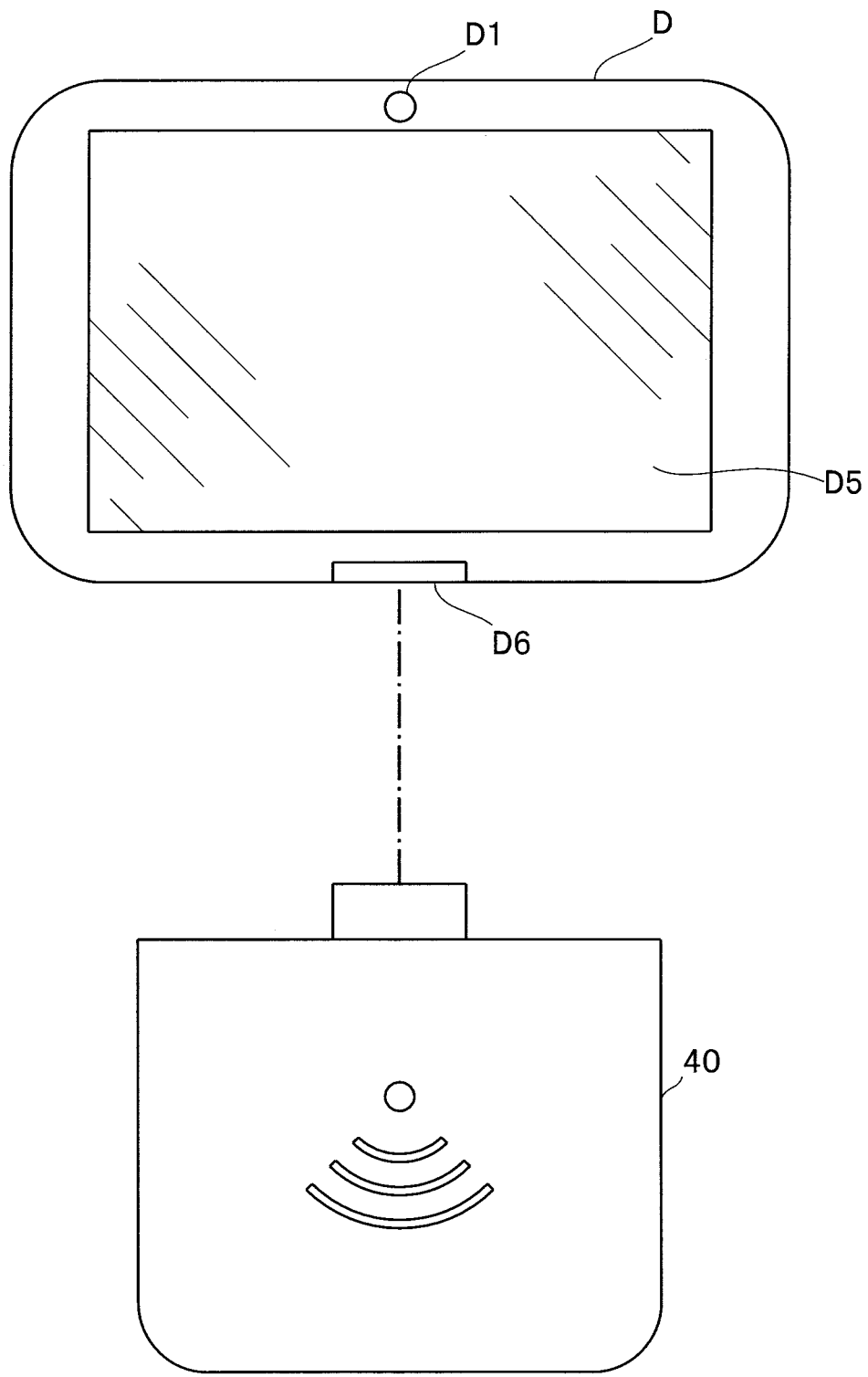
FIG. 7 is an explanatory diagram of a reading apparatus that is removable from the observation terminal.

The external connection connector D6 electrically connects the observation terminal D to an external apparatus. As the external connection connector DC, a USB outlet may be cited as an example. For example, as shown in FIG. 7, the external connection connector D6 may connect a removable RFID reading apparatus 40 as an external apparatus.

The gyrosensor D7 is configured by a piezoelectric element, a silicon resonator or the like, and detects an angular velocity that is caused by a change in an orientation or the like of the observation terminal D. The gyrosensor D7 outputs the detected angular velocity to the control unit D3.

Next, a positioning state determination method for the endoscope E performed by the endoscope reprocessor 1 having such a configuration will be described. For example, determination of a positioning state of the endoscope E is performed according to a flowchart of a positioning state determination routine shown in FIG. 8. The positioning state determination routine is performed by the control unit D3 of the observation terminal D, for example, after the endoscope E is set in the treatment tank 31 by the user. However, the present invention is not limited to such a case, and determination of the positioning state may be performed by an external apparatus, as described above. In other words, a determination unit according to the present invention may be integrated with or separate from the observation terminal D.

FIRST EXAMPLE

When the routine starts, the observation unit acquires image information (S103, an observation step).

Figure 16:
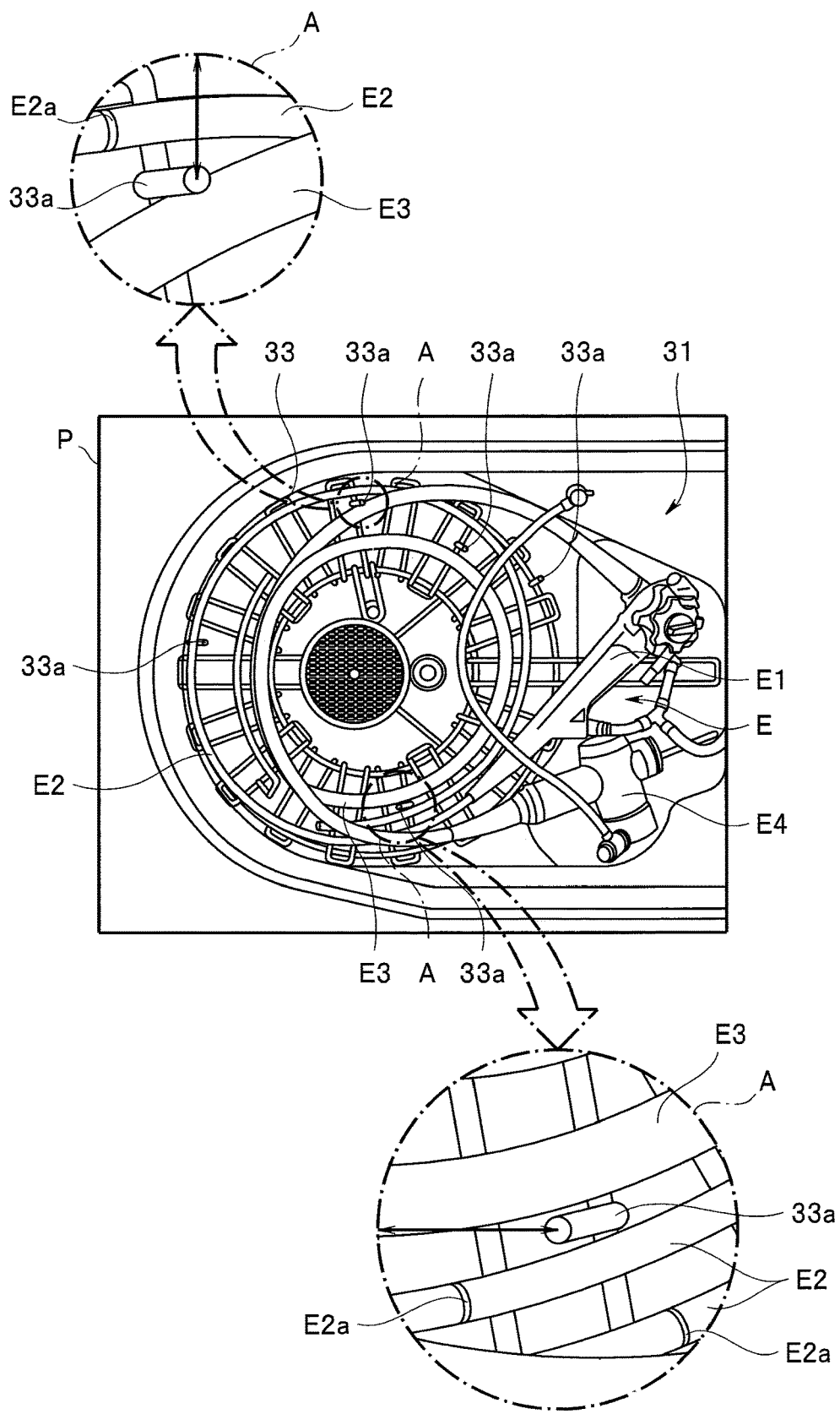
FIG. 16 is an explanatory diagram showing an example of the specific parts of the endoscope present within the evaluation regions.

After the observation step, the determination unit that determines a positioning state, such as the control unit D3, determines whether the positioning state is appropriate or inappropriate, based on the image information and according to an index indicating whether a predetermined part E2*a* of the endoscope is included in a predetermined range A including a predetermined part 33*a* inside the treatment tank as shown in FIG. 16 (S108, a determination step).

In FIG. 16, the pin 33*a* of the holding net is shown as the predetermined part inside the treatment tank, but the present invention is not limited to such a case, and any object that is at a fixed position inside the treatment tank 31 may be used. For example, as the predetermined part inside the treatment tank, the pin 33*a* of the holding net, the hook 33*d* of the holding net, the cleaning case 34, the water level gauge 35, the medicinal solution nozzle 36, a temperature gauge, not shown, or the like may be used.

Figure 15:
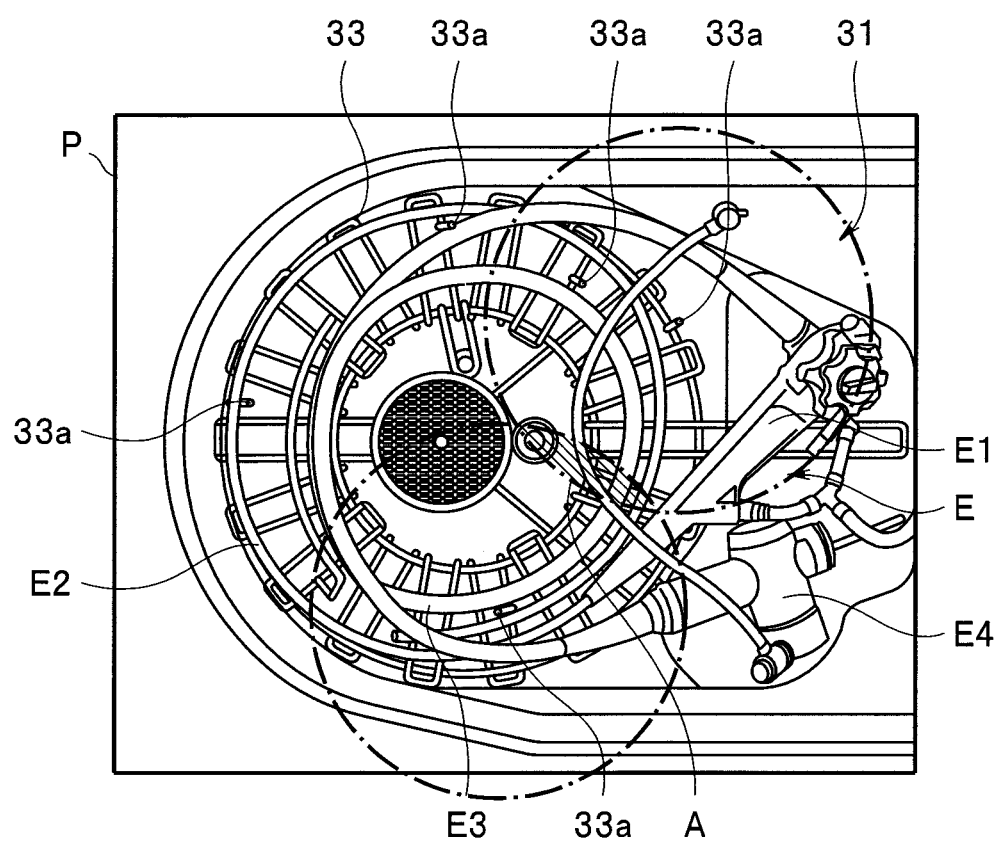
FIG. 15 is an explanatory diagram showing an example of evaluation regions set based on two index pins.

FIG. 16 shows the predetermined range A to have a circular shape, but the present invention is not limited to such a case, and the predetermined range A may have other shapes such as an oval shape or a polygonal shape, or may be an overlapped portion of two figures as shown in FIG. 15. Furthermore, a size and a shape of the predetermined range A may be changed according to endoscope information such as type. Details of an acquisition method of the endoscope information will be given in a first modification of the first example. It suffices if there is at least one predetermined range A, and the predetermined range A may be provided at a plurality of parts as shown in FIG. 16.

In FIG. 16, a scale line on the endoscope is shown as an example of the predetermined part E2a of the endoscope, but the present invention is not limited to such a case, and any part forming the endoscope, such as an endoscope distal end, may be used.

After the determination step, the notification unit notifies the result of determination (S111, a notification step). The notification unit may notify both of a case of "appropriate positioning" and a case of "inappropriate positioning", or may notify only the case of "inappropriate positioning". In the case of the latter, the reprocessor 1 permits reprocessing in the case where the result of determination is "appropriate positioning" (S110). Permission here may mean automatic start of reprocessing by the reprocessor, or may be enabling of operation of reprocessing start using the operation unit 24 of the reprocessor.

As the notification unit, any apparatus that is capable of communicating with the determination unit and that includes a notification function may be used as appropriate. For example, the display unit 23 provided to the reprocessor 21, or the display unit D5 of the observation terminal D may be used.

Notification by the notification unit may be notification by visual information, notification by audio information, or notification by other methods.

First Modification of First Example

Before acquiring the image information (S103, the observation step), the control unit D3 may acquire the endoscope information of the endoscope E in step S101, or may check whether the endoscope information of the endoscope E is acquired or not.

The endoscope information here may be acquired by causing the reading apparatus 27a provided to the reprocessor main body 21 to read an RFID tag provided on the scope connector E4 or the like of the endoscope E, for example. In other words, when the user brings the scope connector E4 or the like close to the reading apparatus 27a, the control unit 27 acquires information about the endoscope E (the endoscope information) through the reading apparatus 27a. The control unit 27 transmits the acquired endoscope information to the observation terminal D by wireless communication between the communication unit 26 and the communication unit D4. The control unit D3 thus acquires the endoscope information.

In FIGS. 1 and 2, the reading apparatus 27a is disposed outside the treatment tank 31, but the present invention is not limited to such a case, and the reading apparatus 27a may alternatively be disposed inside the treatment tank 31.

Alternatively, in the case where the reading apparatus 40 is connected to the external connection connector D6, the control unit D3 may directly acquire information about the endoscope E by the user bringing the scope connector E4 or the like close to the reading apparatus 40. Note that the reading apparatus may also be embedded in the observation terminal D in advance.

Alternatively, the control unit D3 may acquire the endoscope information by picking up an image of the specific part of the endoscope E by the observation unit D1 or the observation D2 and identifying a model or the like of the endoscope E based on the shape identified by image recognition or the like or an identification number.

Alternatively, the control unit D3 may acquire the endoscope information through manual input or voice input of the endoscope information by the user.

Alternatively, the control unit D3 may acquire the endoscope information by acquiring information that is inputted to a clinical record in an external apparatus at the time of endoscopic diagnosis.

In step S101, in the case where it is determined that the endoscope information is not acquired, the control unit D3 stays in standby. In the case where it is determined in step S101 that the endoscope information is acquired, the control unit D3 proceeds to a next step.

Second Modification of First Example

The process may proceed from step S101 to Step S102. In step S102, the control unit D3 checks whether there is occurrence of a trigger for starting image pickup of the positioning state of the endoscope E. Alternatively, instead of performing S102, image pickup and determination may be performed constantly.

As the trigger, an orientation of the observation terminal D that is calculated based on an angle or the like from the gyrosensor D7 at the time of the top cover 11 being moved by the user in a closing direction from a fully opened state may be used.

Alternatively, in the case where the user inputs voice to the observation terminal D, the control unit D3 may take a predetermined command recognized by voice recognition as the trigger to start image pickup.

Alternatively, a switch (not shown) that is turned on every time the top cover 11 is rotated by a predetermined angle may be provided to the hinge 11a, and an on signal generated by the switch may be taken as the trigger to start image pickup. In this case, the control unit D3 may receive the signal from the switch provided to the hinge 11a, in a wired or wireless manner.

Alternatively, the control unit D3 may take predetermined operations performed by the user on various switches, such as the foot panel 28, provided to the reprocessor main body 21 as the triggers. In this case, the control unit D3 may receive a predetermined signal generated at the reprocessor main body 21 by an operation by the user, by wireless communication or wired communication between the communication unit 26 and the communication unit D4.

Alternatively, the control unit D3 may take a pressing operation of the user on an image pickup button displayed on the display unit D5 of the observation terminal D as the trigger.

In the case where it is determined in step S102 that there is no occurrence of the trigger to start image pickup, the control unit D3 stays in standby. In the case where it is determined in step S102 that there is occurrence of the trigger to start image pickup, the control unit D3 proceeds to step S103, and picks up an image of the positioning state of the endoscope E positioned inside the treatment tank 31, by the observation unit D1 or the observation unit D2, and acquires the observation image P (the observation step).

Third Modification of First Example

In the first example, it suffices if there is at least one type of observation image, and the observation terminal D may pick up a plurality of observation images of different types. Various image pickup methods may be used to acquire the plurality of observation images P.

As the method of picking up a plurality of observation images of different types, image pickup may be performed using light with predetermined wavelengths (first and second wavelengths) that are different from each other. As described above, the wavelength here is not limited to visible light, and may be far infrared light, infrared light, or ultraviolet light. When the wavelengths are different from each other, differences are caused in relation to an amount of reflection from a subject and a periphery of the subject and a position of reflection, and thus, a poor image due to halation may be excluded from targets of determination by comparing the observation images with different wavelengths.

As the method of obtaining the plurality of observation images P of different types, for example, image pickup of inside of the treatment tank 31 may be performed from different angles. For example, it is possible to obtain images of inside of the treatment tank 31 that are picked up from different angles, by setting the endoscope E in the treatment tank 31, and acquiring the observation image two or more times from before closing of the top cover 11 to after the top cover 11 is closed. For example, by using the gyrosensor disposed on the observation terminal D or the top cover 11 as described above, the control unit D3 may cause the trigger to start image pickup to occur at each timing when the observation terminal D is changed to a predetermined angle set in advance according to movement of the top cover 11. In this case, the observation terminal D or the endoscope reprocessor 1 may guide the user through voice such that a speed of closing the top cover is not too fast, or a known mechanism for preventing the hinge 11*a* from closing too fast may be installed.

Figure 8:
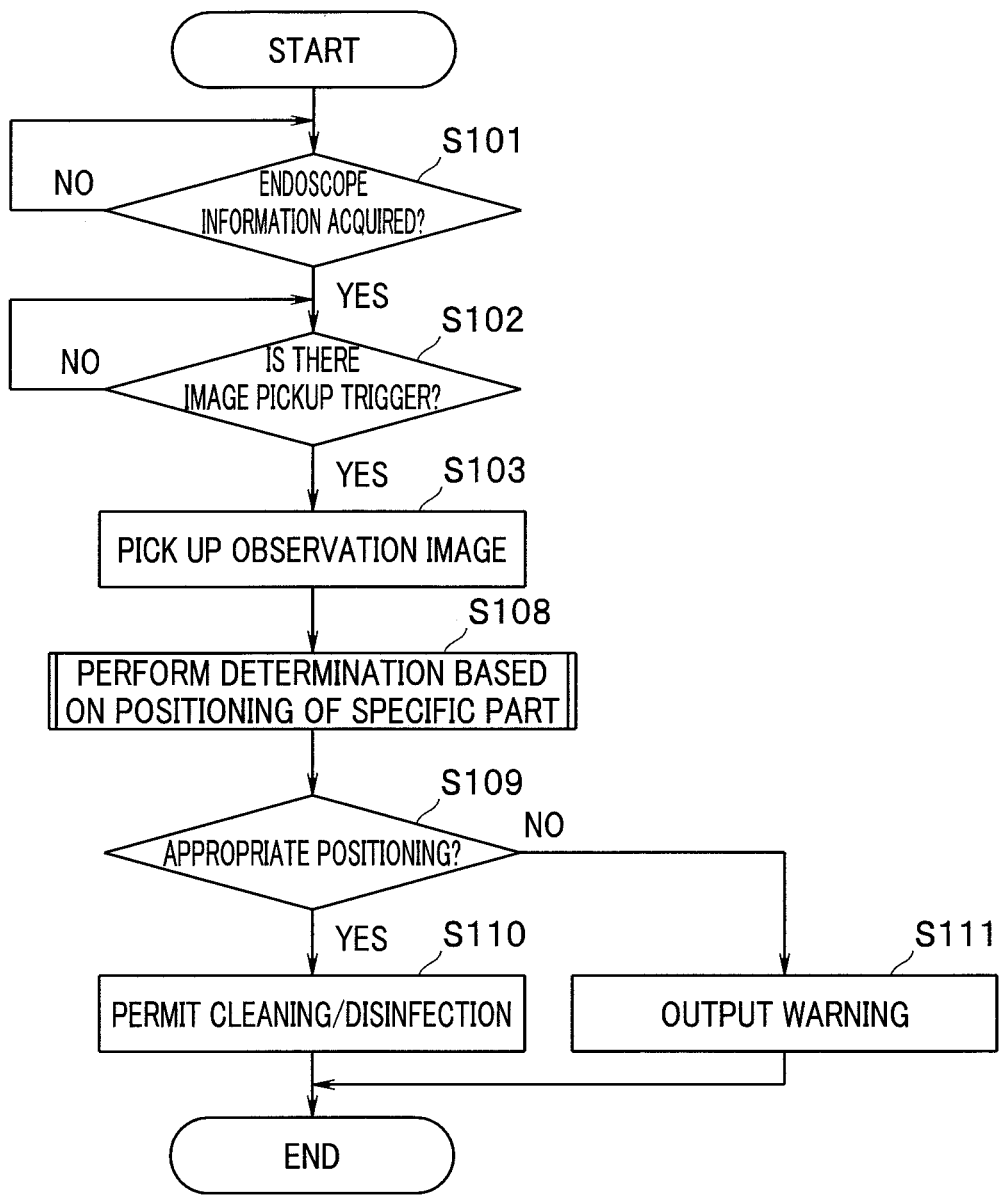
FIG. 8 is a flowchart showing a positioning state determination routine for the endoscope.
Figure 9:
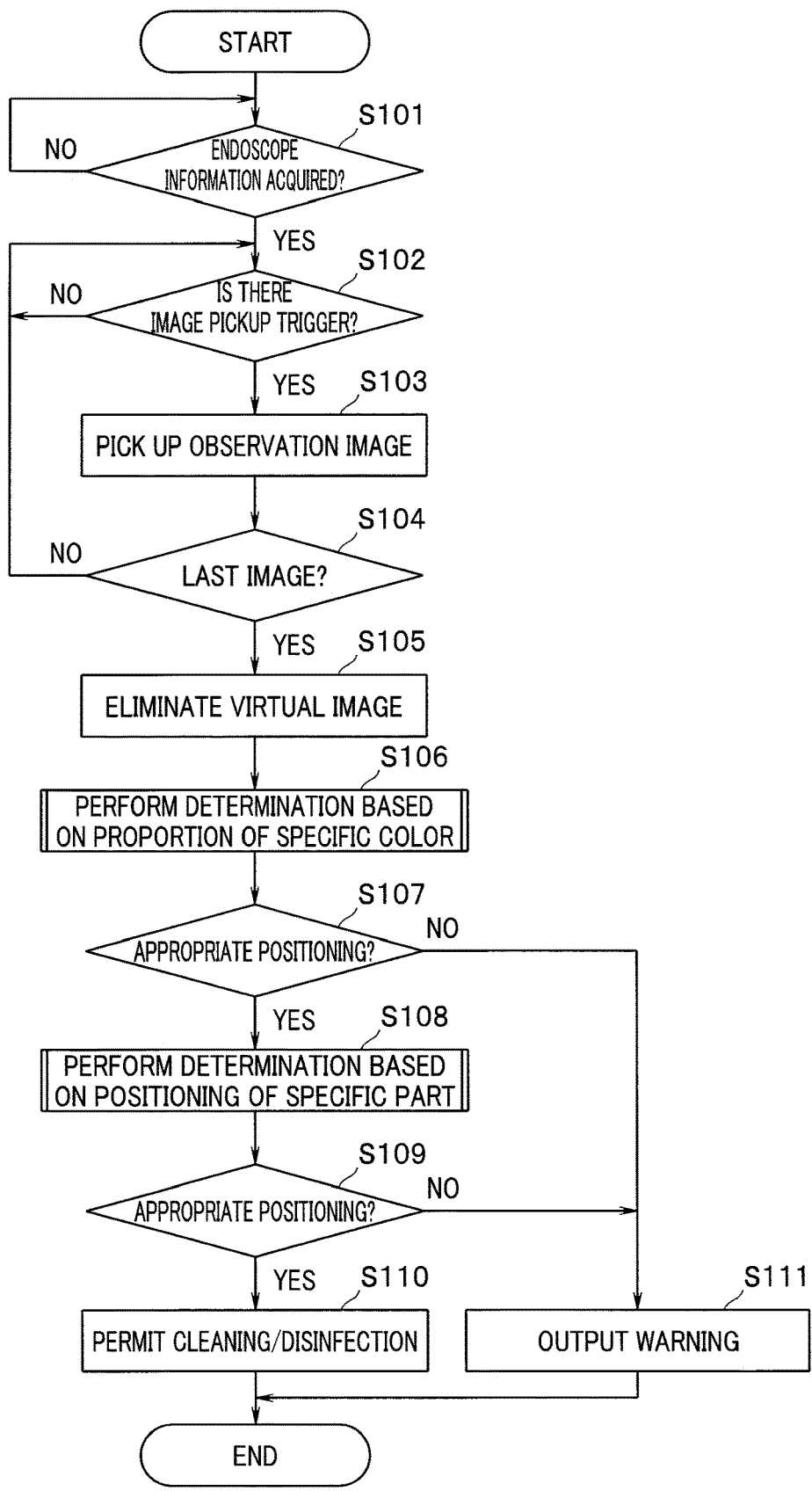
FIG. 9 is a flowchart showing the positioning state determination routine for the endoscope.
Figure 14:
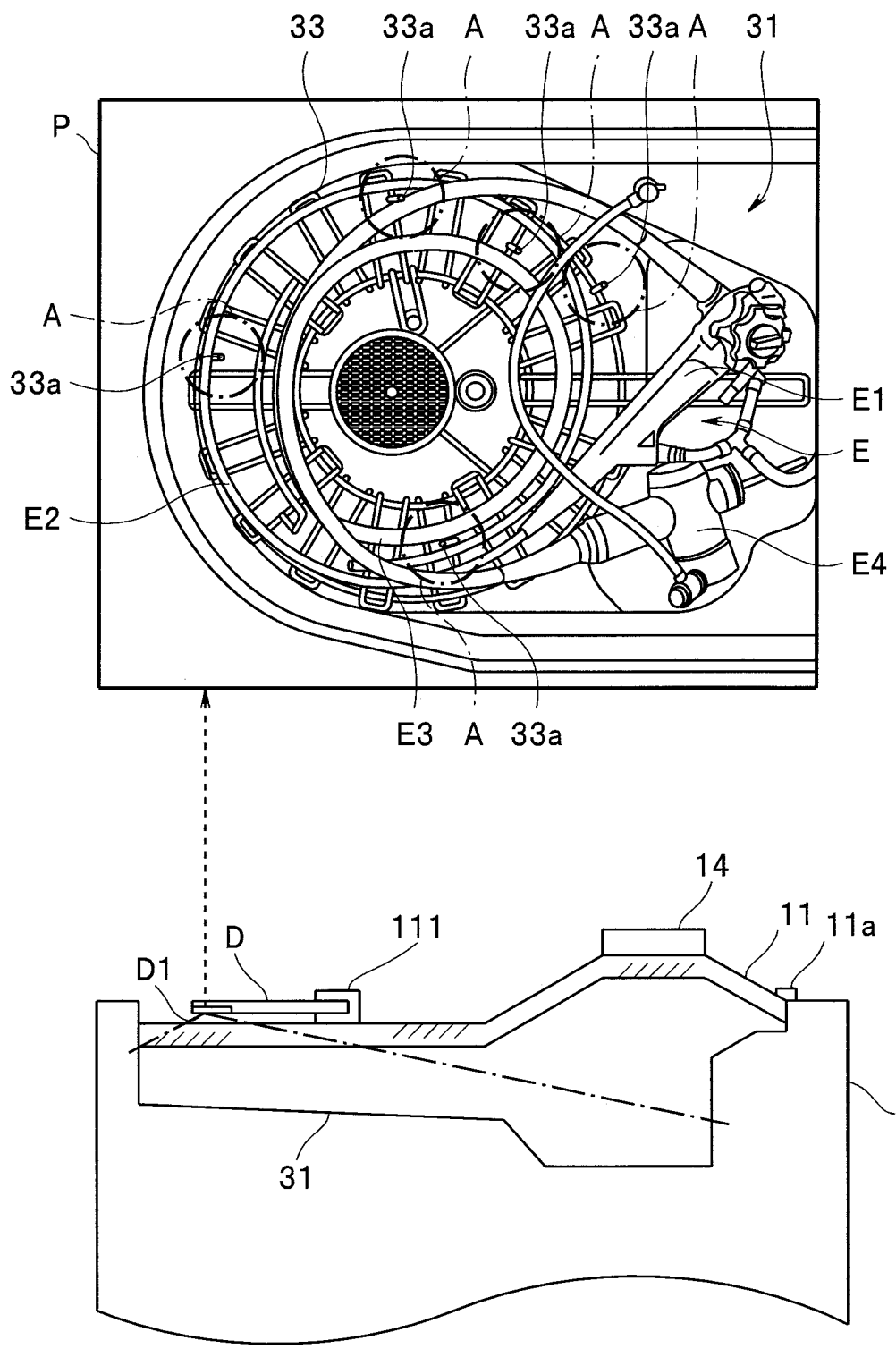
FIG. 14 is an explanatory diagram showing an example of a relationship between a state where the top cover is fully closed and the observation image.

A process for obtaining the plurality of observation images P of different types as described above may be performed based on a flowchart shown in FIG. 9, for example. Note that in FIG. 9, same processes as in FIG. 8 are denoted by same step numbers. When the process proceeds from step S103 to S104, the control unit D3 checks whether the observation image P picked up in step S103 is a last image. The last image here is an image that is picked up in a state where the top cover 11 is fully closed (see FIG. 14). Note that in the present embodiment, the last image is an image that is picked up in a state where the treatment tank 31 is squarely faced.

Then, in the case where it is determined in step S104 that the observation image P that is currently picked up is not the last image, the control unit D3 returns to step S102. In the case where it is determined in step S104 that the observation image P that is currently picked up is the last image, the control unit D3 proceeds to step S105. Note that determination of whether the observation image P is the last image or not may be performed by detecting the state of the hinge 11*a* by the endoscope reprocessor 1 and by transmitting a detected signal to the observation terminal D.

Through repetition of the processes from step S102 to step S104 as described above, the control unit D3 acquires a plurality of (at least two) observation images P picked up under different conditions, between before the top cover 11 is closed and after the top cover 11 is closed.

When the process proceeds from step S104 to step S105, the control unit D3 eliminates a poor image or selects one image for determination by comparing the plurality of observation images P that are acquired. In other words, in the case where the treatment tank 31 is made from a material such as stainless steel, the insertion section E2 or the like of the endoscope E may be reflected on a surface of the treatment tank 31 depending on an angle at which the observation image P is picked up and may appear as a virtual image in the observation image P. Furthermore, when light from a room lamp or the like is reflected on the treatment tank and halation is shown on the image, an endoscope image may be partially chipped. Accordingly, the control unit D3 may eliminate a poor image among the observation images P from determination targets by comparing the observation images P picked up at respective angles.

Fourth Modification of First Example

Figure 11:
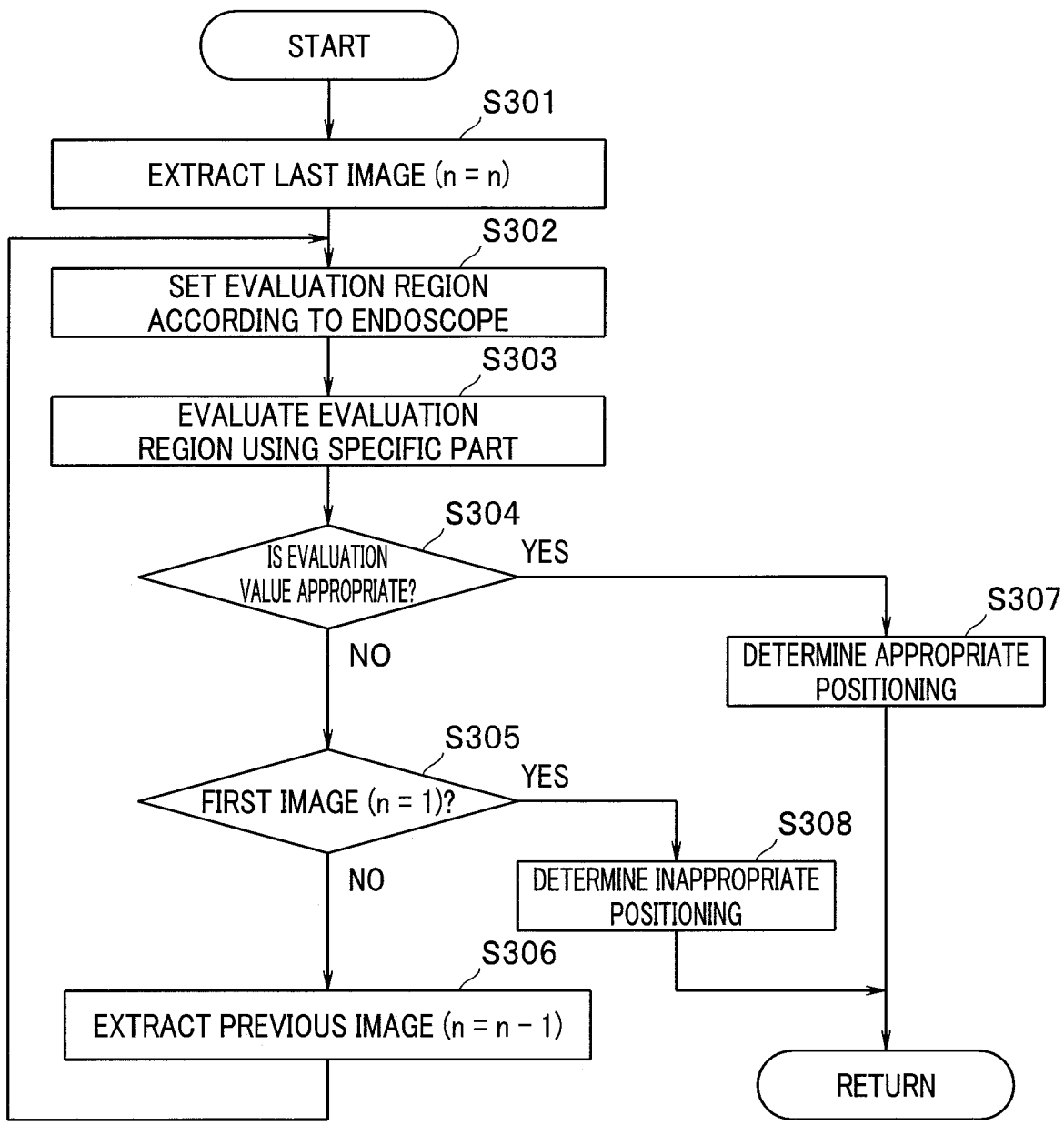
FIG. 11 is a flowchart showing a positioning state determination subroutine for the endoscope that is based on positioning of a specific part.
Figure 12:
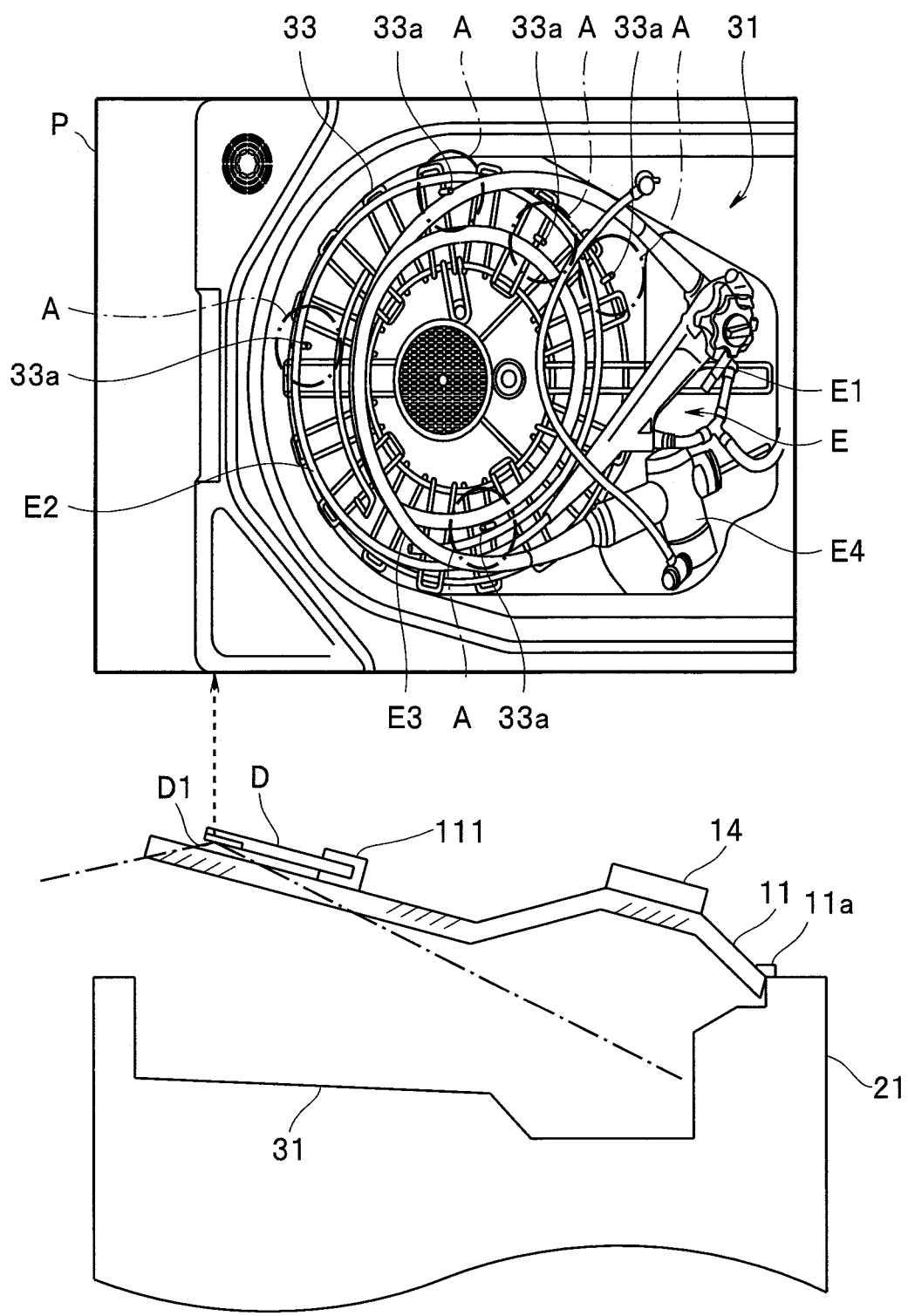
FIG. 12 is an explanatory diagram showing an example of a relationship between a state where a top cover is closed halfway and an observation image.
Figure 13:
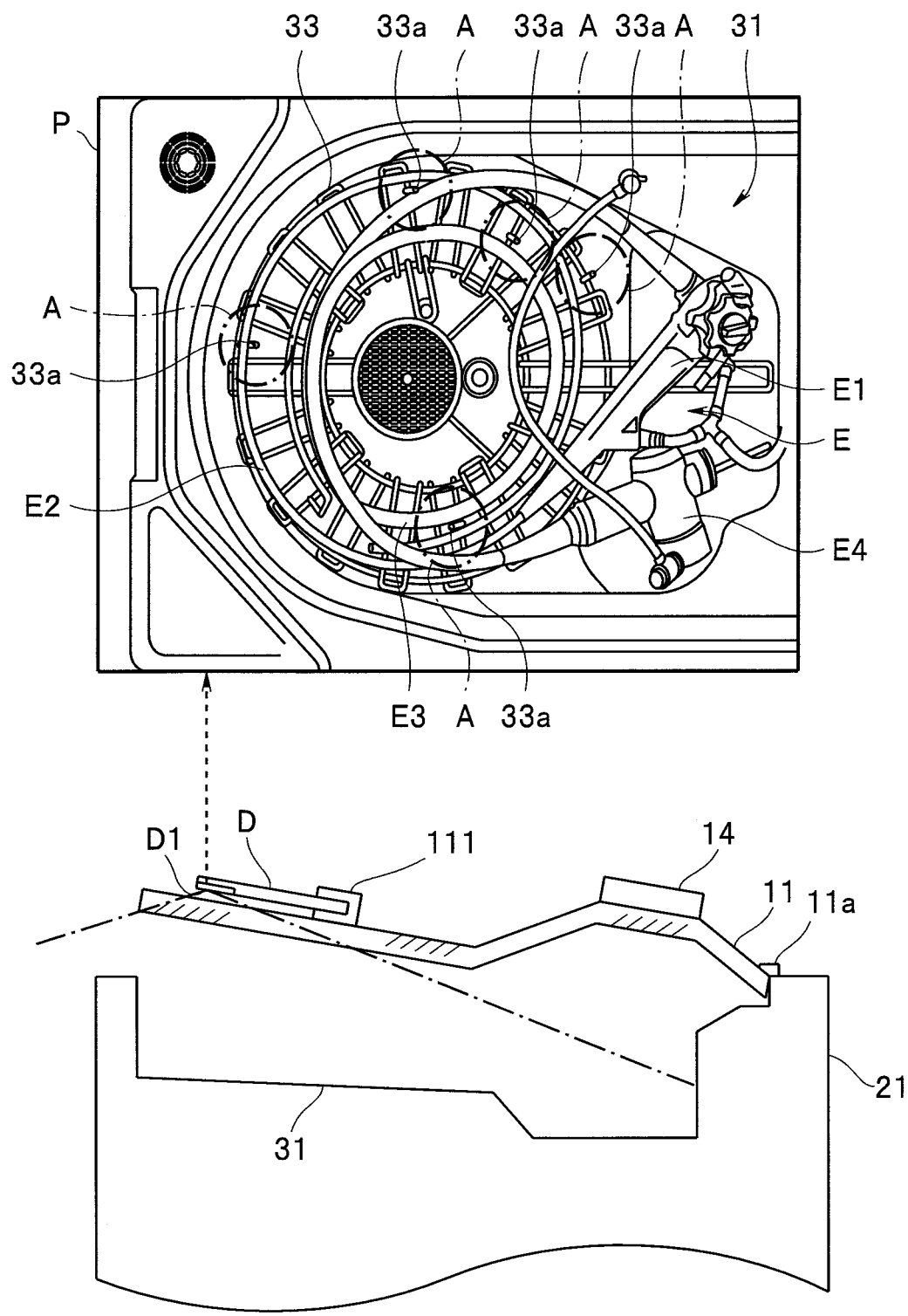
FIG. 13 is an explanatory diagram showing an example of the relationship between the state where the top cover is closed halfway and the observation image.

More specifically, the process in step S108 in the first example may be performed according to a subroutine shown in FIG. 11, for example.

In other words, the control unit D3 extracts an image that is last acquired from among the plurality of observation images P that are acquired (S301).

When the image is extracted, the control unit D3 sets, on the extracted image, one or more predetermined ranges A as evaluation regions, according to the type or the like of the endoscope E (S302).

Next, as described in the example described above, the control unit D3 performs evaluation of the predetermined range A (S303).

When, as a result, an evaluation value is appropriate for every predetermined range A, the control unit D3 determines that the endoscope E is in an appropriate positioning state (S307), and exits the subroutine.

In the case where the evaluation value for at least one predetermined range A is not appropriate, the control unit D3 extracts an image that is acquired immediately before the image that is currently extracted (S306), and returns to the process in step S302.

In the case where the currently extracted image is an image that is acquired first (in the case of "YES" in the determination in S305), the control unit D3 determines that the endoscope E positioned in the treatment tank 31 is in an inappropriate positioning state, and exits the subroutine.

SECOND EXAMPLE

In addition to determination based on positioning of the specific part (S108) described in the first example, a determination method different from S108 may also be performed.

For example, as shown in FIG. 9, determination of whether the endoscope E is appropriately positioned inside the treatment tank 31 may be performed after step S105, based on a proportion of a specific color in the observation image (S106).

Figure 10:
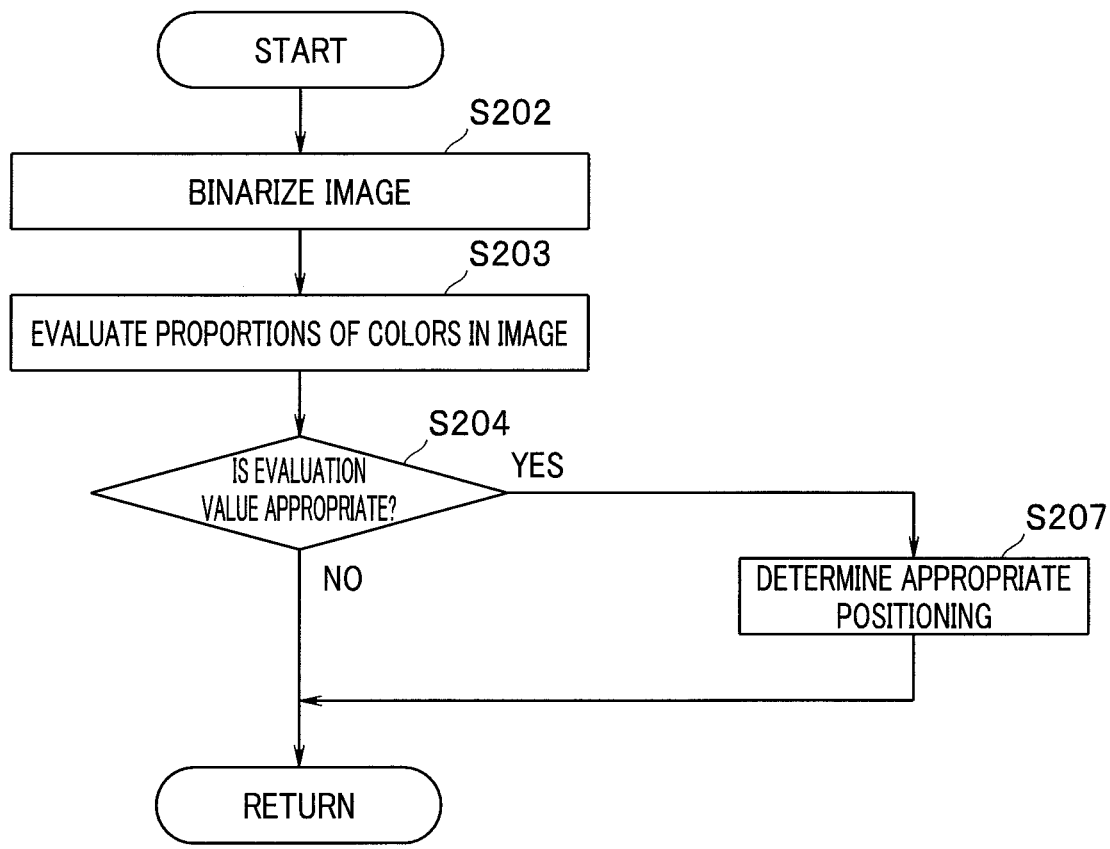
FIG. 10 is a flowchart showing a positioning state determination subroutine for the endoscope that is based on a proportion of a specific color.

Positioning state determination regarding the endoscope based on the proportion of a specific color is performed according to a subroutine shown in FIG. 10, for example. When the subroutine is started, the control unit D3 extracts the observation image P that is acquired by the process in step S103.

For example, in the case where the insertion section E2 and the like of the endoscope E are black and other colors of the treatment tank 31 and the like are other than black, when the observation image P of the evaluation region A showing the insertion section E2 and the treatment tank 31 is binarized (S202), proportions of the insertion section E2 and the treatment tank 31 in each evaluation region A may be roughly grasped by obtaining an evaluation value by evaluating a ratio of the two colors in the image. Accordingly, by determining in advance as thresholds the ratios of the two colors when various endoscopes E (the insertion sections E2) are appropriately positioned, the control unit D3 may perform evaluation as to Whether the endoscope E is appropriately positioned in each evaluation region A, by comparing each threshold and each evaluation value (S203). The color of the endoscope in the image and colors other than the color of the endoscope may be selected as appropriate, and setting may be performed by a binarization process such that display is performed in black when at or greater than the threshold and in white when the threshold is not reached, for example.

Determination based on binarization may be performed on the entire image that is picked up, or may be performed on the predetermined range in the image. In the case of performance on the predetermined range, binarization may be performed on a predetermined range extending outward from a center of the image, or may be performed on a region of a predetermined range from a specific index.

After proceeding from step S203 to step S204, the control unit D3 checks whether the evaluation value is appropriate or not. A determination method of appropriate/inappropriate may be set as appropriate according to the type of the endoscope, the threshold regarding binarization, or the like. For example, appropriate positioning is determined in the case where the proportion of the color of the endoscope is equal to or smaller than a predetermined proportion.

Then, in the case where the evaluation value is determined to be appropriate, the control unit D3 may proceed to step S207 as shown in FIG. 10, and may exit the subroutine after determining that the endoscope E is appropriately positioned inside the treatment tank 31. However, the present invention is not limited to such a case, and the flow may be such that S108 is performed after it is determined in S106 that positioning of the endoscope is appropriate, and such that final determination is made by combining results of S106 and S108.

After proceeding from step S106 to S107 in a main routine in FIG. 9, the control unit D3 checks in step S107 whether it is determined that the endoscope E is appropriately positioned inside the treatment tank 31.

Then, in the case where it is determined by the process in step S106 that positioning is not appropriate, the control unit D3 proceeds from step S107 to step S111, and issues a warning via the display unit 23 of the reprocessor main body 21 or the display unit D5 of the observation terminal D, and exits the routine.

In the case where it is determined by the process in step S106 that positioning is appropriate, the control unit D3 proceeds from step S107 to step S108 described in the first example.

THIRD EXAMPLE

In the case where the positioning state is inappropriate, the notification unit may, after the first example or the second example, notify information for making the positioning state appropriate.

Notification of information for making the positioning state appropriate may be by visual information, audio information, or other methods. As notification by visual information, a method of showing a correct positioning mode on the notification unit, a method of showing next to each other a part that is actually erroneously positioned and a sample image of a correct positioning mode, or the like may be cited as an example. As notification by audio information, a method of leading the user to correct positioning by guiding a position of a hand may be cited as an example.

FOURTH EXAMPLE

Figure 18:
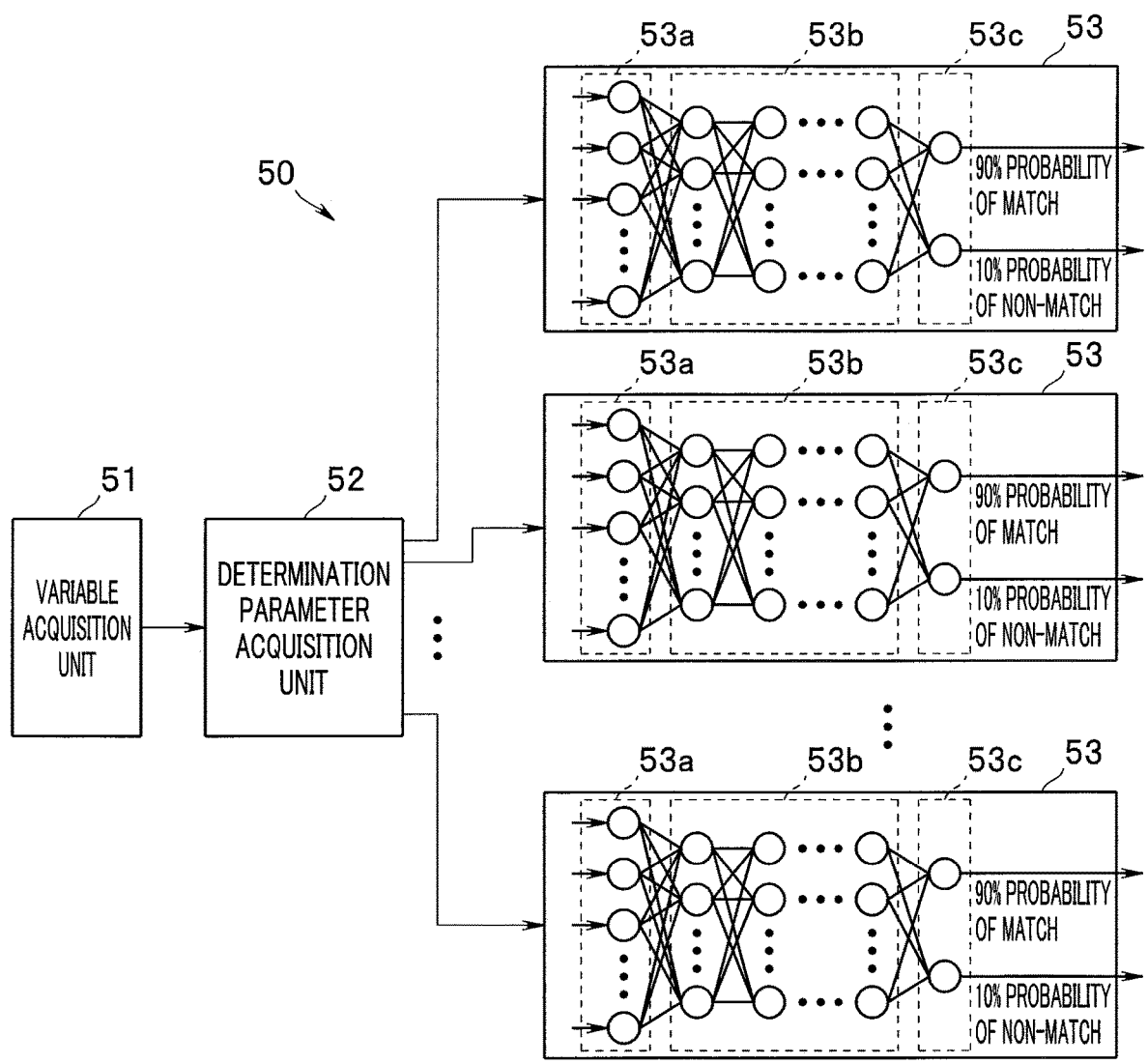
FIG. 18 is a configuration diagram of a determination system including a neural network according to a second modification.

Determination of the positioning state of the endoscope E may also be performed using a determination system 50 including a learned neural network. An example of the determination system that uses a neural network is shown in FIG. 18.

For example, the determination system 50 is constructed in the control unit D3. The determination system 50 includes a variable acquisition unit 51, a determination parameter acquisition unit 52, and a plurality of neural networks 53 as the determination units.

For example, a variable group including the type of the endoscope E, type of the endoscope reprocessor 1, type of the observation terminal D, a position of the observation unit when the observation terminal D is disposed, type of the observation unit, or the number of endoscopes E that are positioned inside the treatment tank 31 is inputted to the variable acquisition unit 51. Note that not all the variables forming the variable group have to be inputted to the variable acquisition unit 51, and it suffices if the variable that is inputted to the variable acquisition unit 51 is at least one type that is selected from the variable group.

For example, the determination parameter acquisition unit 52 generates, and outputs to the corresponding neural network 53, a determination parameter that is associated with the variable that is inputted to the variable acquisition unit 51. In other words, the determination parameter acquisition unit 52 specifies at least one corresponding neural network 53 based on the variable group, and outputs the determination parameter to the neural network 53, for example. As the determination parameter to be outputted to the neural network 53, pixel data of a detection range A set on the observation image P based on the variable group may be used, for example.

Each neural network 53 includes an input layer 53a to which the determination parameter from the determination parameter acquisition unit 52 is inputted, an intermediate layer 53b where calculation is performed on the determination parameter that is inputted to the input layer 53a, and an output layer 53c that outputs a calculation result from the intermediate layer 53b.

The intermediate layer 53b here includes an array of a plurality of artificial neurons. A rule of calculation that is performed between input and output, a plurality of weighting coefficients used in the calculation, and the like are set in each artificial neuron by machine learning performed in advance.

When the determination parameter is inputted to the input layer 53a, the intermediate layer 53b performs calculation at each artificial neuron and thus obtains, in relation to the detection range A, a 90% probability of match (in other words, a 90% probability that positioning of the endoscope E is appropriate) or a 10% probability of non-match (in other words, a 10% probability that positioning of the endoscope E is inappropriate), for example. The calculation result is then outputted by the output layer 53c.

According to such a configuration, determination of whether the endoscope E is positioned in an appropriate positioning state in the treatment tank 31 of the endoscope reprocessor 1 may be performed accurately.

Note that in the embodiment described above, the control unit D3 of the observation terminal D is described to perform the first determination and the second determination and the like, but the present invention is not limited to such a case, and determination may also be performed by the control unit 27 provided to the endoscope reprocessor 1 or the like, for example.

Furthermore, the control unit as the control apparatus may be implemented by a computer including one or more processors, a logic circuit, a memory, an input/output interface, a computer-readable recording medium and the like. In this case, the control unit may be implemented by recording a program for implementing a function of each structural element or entire main body unit in a non-transitory recording medium, causing a computer system to read the program, and executing the recorded program. For example, the processor is at least one of a CPU (central processing unit), a DSP (digital signal processor), or a GPU (graphics processing unit). For example, the logic circuit is at least one of an ASIC (application specific integrated circuit) and an FPGA (field-programmable gate array).

Furthermore, the present invention is not limited to the embodiment described above, and various modifications and changes may of course be made.

What is claimed is:

1. A control apparatus comprising:
one or more processors comprising hardware, wherein the one or more processors are configured to:
 acquire an image showing an endoscope positioned in an endoscope reprocessor;
 detect, in the image, a pin of a holding net disposed inside a treatment tank of the endoscope reprocessor and a scale line of the endoscope; and
 perform a determination, based on the image, of whether the scale line of the endoscope is included in a predetermined range from the pin of the holding net.

2. The control apparatus according to claim 1,
wherein the one or more processors are configured to:
 perform a determination that a positioning state of the endoscope in the endoscope reprocessor is a predetermined positioning state in a case where the scale line of the endoscope is determined to be included in the predetermined range from the pin of the holding net; and
 output a signal for notifying a result of the determination that the positioning state is the predetermined positioning state.

3. The control apparatus according to claim 1,
wherein the one or more processors are configured to:
 acquire a plurality of images;
 eliminate one or more images in which the endoscope is shown as a virtual image from the plurality of images; and
 acquire the image showing the endoscope positioned in the endoscope reprocessor from one or more remaining images that were not eliminated from the plurality of images.

4. The control apparatus according to claim 1,
wherein the one or more processors are configured to:
 acquire a plurality of images picked up from different angles according to opening/closing of a cover that is provided with one end being capable of being opened/closed and another end being fixed to the endoscope reprocessor; and
 acquire the image showing the endoscope positioned in the endoscope reprocessor from the plurality of images.

5. The control apparatus according to claim 1,
wherein the one or more processors are configured to:
 acquire a plurality of images showing the endoscope positioned in the endoscope reprocessor; and
 perform the determination of whether the scale line of the endoscope is included in the predetermined range from the pin of the holding net, in order from one of the plurality of images that is acquired at a later time in a time series.

6. The control apparatus according to claim 5,
wherein a last one of the plurality of images, in the time series, is an image that is picked up in a state where a cover that is provided with one end being capable of being opened/closed and another end being fixed to the endoscope reprocessor is closed, and
wherein the one or more processors are configured to perform the determination of whether the scale line of the endoscope is included in the predetermined range from the pin of the holding net in order from the last one of the plurality of images.

7. The control apparatus according to claim 1,
wherein the one or more processors are configured to:
 acquire endoscope information; and
 change at least one of the pin of the holding net and the scale line of the endoscope based on the endoscope information.

8. The control apparatus according to claim 1,
wherein the one or more processors are configured to:
 acquire a plurality of images including an image that is picked up at a first wavelength and an image that is picked up at a second wavelength different from the first wavelength;
 perform a comparison of the plurality of images; and
 acquire the image showing the endoscope positioned in the endoscope reprocessor based on a result of the comparison.

9. The control apparatus according to claim 1,
wherein the one or more processors are configured to:
 calculate a proportion of a specific color of at least a part of the image; and
 perform a comparison of the proportion of the specific color of the at least the part of the image with a threshold.

10. The control apparatus according to claim 9,
wherein the one or more processors are configured to:
 acquire endoscope information regarding the endoscope; and
 change the threshold based on the endoscope information.

11. The control apparatus according to claim 1,
wherein the one or more processors are configured to:
 input the image to a machine-learned model; and
 perform the determination of whether the scale line of the endoscope is included in the predetermined range from the pin of the holding net based on an output of the machine-learned model.

12. An endoscope positioning state determination method comprising:
acquiring an image showing an endoscope positioned in an endoscope reprocessor;
detecting, in the image, a pin of a holding net disposed inside a treatment tank of the endoscope reprocessor and a scale line of the endoscope; and
performing a determination, based on the image, of whether the scale line of the endoscope is included in a predetermined range from the pin of the holding net.

13. The endoscope positioning state determination method according to claim 12, further comprising:

acquiring a plurality of images picked up from different angles according to rotation of a cover that is provided with one end being rotatable and another end being fixed to the endoscope reprocessor.

14. The endoscope positioning state determination method according to claim 13,
wherein the last one of the plurality of images is an image that is picked up in a state where the cover is closed.

15. A non-transitory computer-readable recording medium recording a program for causing a computer to:
acquire an image showing an endoscope positioned in an endoscope reprocessor;
detect, in the image, a pin of a holding net disposed inside a treatment tank of the endoscope reprocessor and a scale line of the endoscope; and
perform a determination, based on the image, of whether the scale line of the endoscope is included in a predetermined range from the pin of the holding net.

16. The control apparatus according to claim 1,
wherein the one or more processors are configured to perform a determination of whether a positioning state of the endoscope in the endoscope reprocessor is a predetermined positioning state based on a result of the determination of whether the scale line of the endoscope is included in the predetermined range from the pin of the holding net.

17. The control apparatus according to claim 1,
wherein the scale line is one of a plurality of scale lines having a plurality of positions when arranged in the endoscope reprocessor.

18. The control apparatus according to claim 1,
wherein the one or more processors are configured to:
perform a determination that a positioning state of the endoscope in the endoscope reprocessor is not a predetermined positioning state in a case where the scale line of the endoscope is determined to be not included in the predetermined range from the pin of the holding net; and
output a signal for notifying a result of the determination that the positioning state is not the predetermined positioning state.

19. The endoscope positioning state determination method according to claim 12, further comprising:
performing a determination of whether a positioning state of the endoscope in the endoscope reprocessor is a predetermined positioning state based on a result of the determination of whether the scale line of the endoscope is included in the predetermined range from the pin of the holding net.

20. The non-transitory computer-readable recording medium according to claim 15, wherein the program causes the computer to:
perform a determination of whether a positioning state of the endoscope in the endoscope reprocessor is a predetermined positioning state based on a result of the determination of whether the scale line of the endoscope is included in the predetermined range from the pin of the holding net.

* * * * *